United States Patent
Satyamurthy et al.

(10) Patent No.: US 8,742,139 B2
(45) Date of Patent: Jun. 3, 2014

(54) NO-CARRIER-ADDED NUCLEOPHILIC [F-18] FLUORINATION OF AROMATIC COMPOUNDS

(75) Inventors: Nagichettiar Satyamurthy, Los Angeles, CA (US); Jorge R. Barrio, Agoura Hills, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 13/263,333

(22) PCT Filed: Apr. 1, 2010

(86) PCT No.: PCT/US2010/001012
§ 371 (c)(1),
(2), (4) Date: Nov. 10, 2011

(87) PCT Pub. No.: WO2010/117435
PCT Pub. Date: Oct. 14, 2010

(65) Prior Publication Data
US 2012/0123120 A1    May 17, 2012

Related U.S. Application Data

(60) Provisional application No. 61/167,832, filed on Apr. 8, 2009.

(51) Int. Cl.
*C07D 319/06*    (2006.01)
(52) U.S. Cl.
CPC .................... *C07D 319/06* (2013.01)
USPC ............ 549/372; 549/417; 544/303; 546/188
(58) Field of Classification Search
USPC .......... 424/1.89; 544/408; 568/306; 549/372, 549/417
See application file for complete search history.

(56) References Cited

FOREIGN PATENT DOCUMENTS

CA    1295549 C    * 2/1992

OTHER PUBLICATIONS

Oxford Dictionary of Chemistry 169 (John Daintith ed., 6th ed., 2008).*
J. Med. Chem. 45, 563-566 (2002).*
V.W. Pike et al., 21 Journal of the Chemical Society, Chemical Communications 2215-2216 (1995).*
E. Malamidou-Xenikaki et al., 68 Journal of Organic Chemistry, 5627-5631 (2003).*
P. Müller et al., Tetrahedron Asymmetry, 779-785, 780 (2003).*
R.M. Moriarty et al., 107 Journal of the American Chemical Society 1375-1378, 1376 (1985).*

* cited by examiner

*Primary Examiner* — Deepak Rao
*Assistant Examiner* — Alexander R Pagano
(74) *Attorney, Agent, or Firm* — Koppel, Patrick, Heybl & Philpott; Michael J. Ram

(57) ABSTRACT

Phenyliodonium ylide derivatives substituted with electron donating as well as electron withdrawing groups on the aromatic ring are shown for use as precursors in aromatic nucleophilic substitution reactions. The iodonium ylide group is substituted by nucleophiles such as halide ions to provide the corresponding haloaryl derivatives. No-carrier-added [F-18] fluoride ion exclusively substitutes the iodonium ylide moiety in these derivatives and provides high specific activity F-18 labeled fluoro derivatives. Protected L-dopa-6-iodonium ylide derivative have been synthesized as a precursors for the preparation of no-carrier-added 6-[F-18]fluoro-L-dopa. The iodonium ylide group in this L-dopa.derivative is nucleophilically substituted by no-carrier-added [F-18]fluoride ion to provide a [F-18]fluoro intermediates which upon acid hydrolysis yielded 6-[F-18]fluoro-L-dopa.

22 Claims, 9 Drawing Sheets

Reagents: a) NaIO$_4$/CH$_3$COONa/(CH$_3$CO)$_2$O/CH$_3$COOH; b) 2,2-Dimethyl-1,3-dioxane-4,6-dione (Meldrum's acid)/Na$_2$CO$_3$; c) 5,5-Dimethyl-1,3-cyclohexanedione (Dimedone)/Na$_2$CO$_3$; d) 1,3-Dimethylbarbituric acid/Na$_2$CO$_3$; e) 4-Hydroxycoumarin/Na$_2$CO$_3$; f) 4-Hydroxy-1-methyl-2(1H)-quinolone/Na$_2$CO$_3$.

a) $R_1 = R_3 = R_4 = H; R_2 = CH_3$ b) $R_1 = R_2 = R_4 = CH_3; R_3 = H$ c) $R_1 = R_2 = R_3 = H; R_4 = OCH_3$ d) $R_1 = R_2 = R_4 = H; R_3 = OCH_3$ e) $R_1 = R_3 = R_4 = H; R_2 = OCH_3$ f) $R_1 = R_3 = R_4 = H; R_2 = Br$ g) $R_1 = R_3 = R_4 = H; R_2 = Cl$ h) $R_1 = R_3 = R_4 = H; R_2 = NO_2$

HX = HCl, HBr, CH$_3$COOH, CF$_3$COOH

Reagents: a) LiOH/THF; b) Paraformaldehyde/camphorsulfonic acid/benzene; c) Dimethyldioxirane/CH₃COOH; d) 2,2-Dimethyl-1,3-dioxane-4,6-dione.

Reagents: a) NaBH$_4$/CH$_3$OH; b) CF$_3$COOAg/I$_2$; c) HBr ; d) LDA/(S)-(-)-1-Boc-2-tert-butyl-3-methyl-4-imidazolidinone ; e) BuLi/(2R)-2,5-dihydro-3,6-dimethoxy-2-isopropylpyrazine ;
f) 1)Dimethyldioxirane/CH$_3$COOH; 2) 2,2-Dimethyl-1,3-dioxane-4,6-dione.

NO-CARRIER-ADDED NUCLEOPHILIC [F-18] FLUORINATION OF AROMATIC COMPOUNDS

This is a National Stage Application of PCT/US2010/001012, filed 1 Apr. 2010, published as WO2010/117435, claiming priority of Application Ser. No. 61/167,832, filed 8 Apr. 2009.

BACKGROUND

Incorporation of positron emitting fluorine-18 (half-life=110 min) into aromatic ring systems plays a very important role in the development of novel biomarkers for utilization in Positron Emission Tomography (PET). Two major pathways are commonly used for this process, namely, electrophilic and nucleophilic fluorine substitution reactions.

Electrophilic fluorination reactions can only provide products with low specific activities (ca 1-5 Ci/mmol) because of the unavoidable addition of non-radioactive elemental fluorine (often called carrier fluorine) during the current production techniques for F-18 labeled fluorine. The combination of labeled fluorine and carrier fluorine is referred to as [$^{18}$F] F$_2$. A typical example of electrophilic radiofluorination can be summarized by the following reaction:

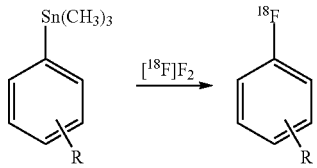

Where R = electron withdrawing groups (e.g. CHO, COOEt, CN, NO$_2$ etc) or electron donating groups (e.g. CH$_3$, OCH$_3$ etc.)

Low specific activity biomarkers prepared by electrophilic aromatic radiofluorination reactions with [F-18]fluorine and reagents derived from it are generally useful for monitoring enzyme-mediated processes (e.g., aromatic amino acid decarboxylase dependent transformation). However, they are unsuitable for investigation of biochemical processes such as receptor systems or enzyme inhibition.

Nucleophilic radiofluorination of aromatic rings, on the other hand, provides products with high specific activity (ca 1,000-10,000 Ci/mmol). Unlike molecular [F-18]fluorine which is obtained in 0.3-0.7 Ci levels, high specific activity [F-18]fluoride ion, which is the fluorinating agent for nucleophilic substitution reactions, is more conveniently prepared in large quantities (1-10 Ci). Facile displacement of certain leaving groups (e.g. nitro and quaternary ammonium moiety) in aromatic systems activated by electron withdrawing substituents (e.g. CHO, COCH$_3$, NO$_2$, CN, COOCH$_3$) by high specific activity [F-18]fluoride ion is well documented and can be depicted as follows:

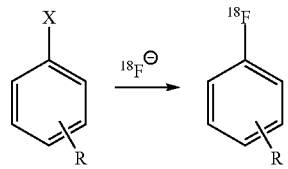

Where R = electron withdrawing groups (e.g. CHO, COOEt, CN, NO$_2$ etc) located at ortho or para position with respect to the group X, and X = NO$_2$ or ⊕N(CH$_3$)$_3$ Simple deactivated aromatic rings, such as the example cited above, provide [F-18]fluorinated products in good radiochemical yields (30-80%). However, as the complexity of the aromatic ring system increases (which is the case with almost all the useful biomarkers) the radiochemical yields obtained by this reaction drops drastically. Further, aromatic compounds lacking electron withdrawing/deactivating substituents (i.e. CHO, CN, NO$_2$ etc) fail to undergo this reaction. Two different routes have been formulated for aromatic nucleophilic fluorination reactions for rings that carry deactivating substituents (e.g. CHO, NO$_2$, CN etc) as well as groups that are electron donating in nature (e.g. CH$_3$, OCH$_3$). The first reaction involves an acid catalyzed thermal decomposition of phenyl triazenes bearing electron donating or electron withdrawing groups on the aromatic ring as shown below:

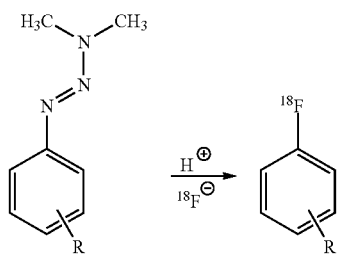

Where R = electron donating groups (e.g. CH$_3$, OCH$_3$ etc) or electron withdrawing (CHO, NO$_2$, CN) group substituted at ortho, meta, para position with respect to the triazene moiety.

The second approach for the nucleophilic fluorination of aryl derivatives substituted with electron donating or electron withdrawing groups involves utilization of iodonium salts as depicted below:

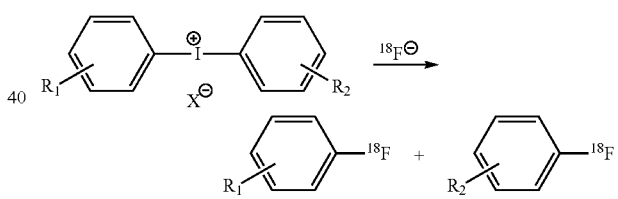

R$_1$ and R$_2$ = electron donating (e.g. CH$_3$, OCH$_3$ etc) or electron withdrawing (CHO, NO$_2$ etc) groups located at ortho, meta or para positions with respect to the iodonium moiety.
X$^\ominus$ = triflate, tosylate or bromide.

While the radiochemical yield for this reaction is generally good with simple substrates, the radiolabeled fluorine (i.e. $^{18}$F) can end up on either of the phenyl rings. Thus, essentially this reaction provides a mixture of two F-18 labeled products; usually one of them is the desired product while the second one is an unwanted product. The percent distribution of the radiolabeled fluorinated products depends upon the electron donating/electron withdrawing nature of the substituent (i.e. R$_1$ and R$_2$) on the phenyl rings. In these iodonium salts, the phenyl ring carrying an electron withdrawing group is invariably radiofluorinated in higher yields than its counterpart phenyl ring substituted with an electron donating group. To obviate this shortcoming a new class of iodonium salt having a thiophene ring system has been advanced. Reaction of this thiophene

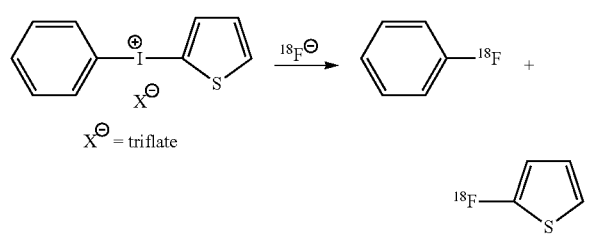

iodonium salt with no carrier added F-18 fluoride ion has been reported to yield [F-18]fluorobenzene as the single radiolabeled product (T. L. Ross, J. Ermert, C. Hocke and H. H. Coenen, "Nucleophilic $^{18}$F-Fluorination of Heteroaromatic Iodonium Salts with No-Carrier-Added [$^{18}$F]Fluoride." *J. Am. Chem. Soc.*, 129, pp 8018-8025 (2007)). However, later careful analysis of this reaction mixture has revealed that both [F-18]fluorobenzene and 2-[F-18]fluorothiophene were produced (M. Carroll, C. Jones and S.-L. Tang, "Fluoridation of 2-thienyliodonium salts". *J. Label. Compd. Radiopharm.*, 50, pp 450-451 (2007)).

Thus, there is a great need for fluorination reactions and particularly for nucleophilic aromatic fluorination reaction conditions that are suitable for the preparation of F-18 labeled biomarkers having a variety of substituents, including electron donating groups. Using such reactions will make many different biomarkers easily accessible and will facilitate development and use of molecular imaging probes for PET. It is also anticipated that similar reactions with various nucleophiles would expand the utility of the approach to a multitude of labeled and unlabeled molecules.

SUMMARY

A novel aromatic nucleophilic halogenation reaction which proceeds without the addition or inclusion of an ion carrier is described. In particular, a fluorination reaction which proceeds without the addition or inclusion of an [F-18] fluoride ion carrier is set forth. In a preferred procedure this "no-carrier-added" [F-18] fluoride ion is reacted with a phenyliodonium ylide derivative, with the fluoride ion nucleophilically substituting the iodonium ylide group on the aromatic ring, resulting in regiospecific F-18 labeled aromatic compounds. The no-carrier-added [F-18] fluoride ion is produced by proton irradiation of [O-18] water using a cyclotron. The [F-18] fluoride ion is then treated with potassium carbonate and a Kryptofix® ligand and the aqueous solution is evaporated. The residue is further dried using azeotropic distillation with acetonitrile to provide a dried [F-18] fluoride ion in the Kryptofix® structure. Alternatively, no-carrier-added [F-18] CsF or [F-18] tetraalkylammonium fluoride is used instead of [F-18] KF/Kryptofix. The phenyliodonium ylide compound dissolved in DMF is then reacted with the dried [F-18]fluoride ion to form the [F-18] fluoroaryl derivative which is isolated using silica gel column chromatography. These [F-18] fluorinated aromatic compounds can have applications in Positron Emission Tomography (PET).

DETAILED DESCRIPTION

Figure 1:
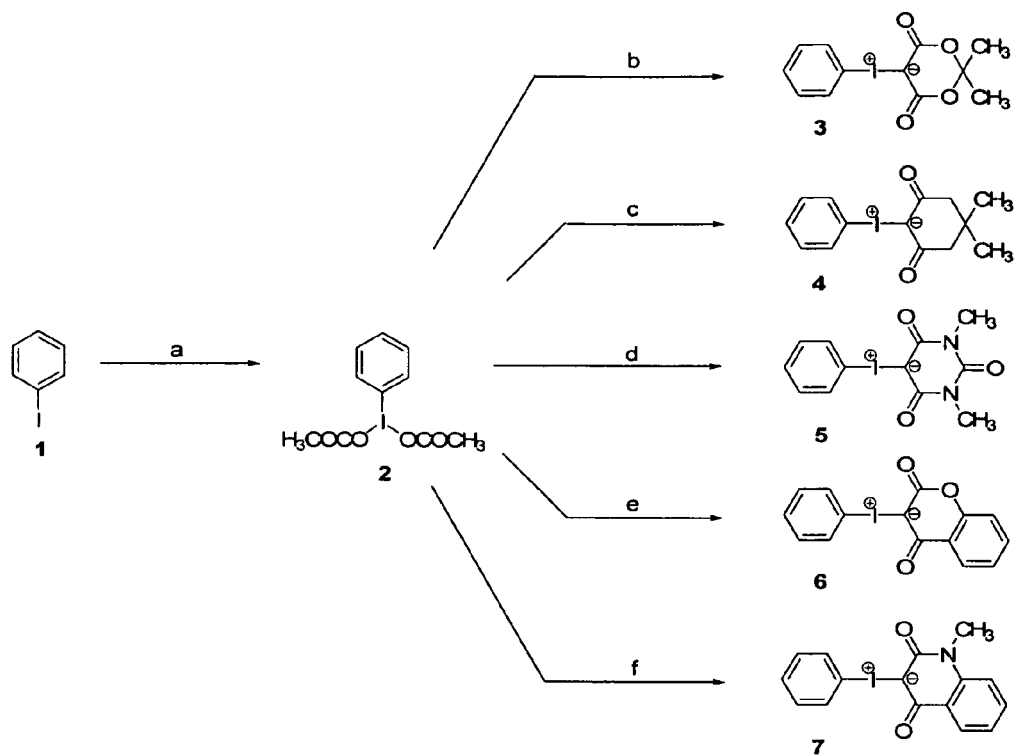
FIG. 1 shows the basic chemical reaction sequence for the preparation of five different phenyliodonium ylides.

The new fluorination reaction developed in this invention utilizes the reaction of phenyliodonium ylides with no-carrier-added [F-18] fluoride ion. Five different unsubstituted phenyliodonium ylides 3-7 shown in FIG. 1 were selected for initial investigation. A general procedure for the synthesis of some of these ylides is known in the prior art (K. Schank and C. Lick, "Ozonolytic Fragmentation of Phenyliodonium □-Diketonates: A Convenient Synthesis of Unsolvated vic-Triketones." *Synthesis*, pp 392-395 (1983)). These derivatives were synthesized by oxidizing iodobenzene (1) with sodium periodate in the presence of sodium acetate and acetic anhydride in acetic acid medium to give diacetoxy iodobenzene (2) which upon reaction with cyclic 1,3-dione analogs provided the corresponding phenyliodonium ylides 3-7 (FIG. 1).

Figure 2:
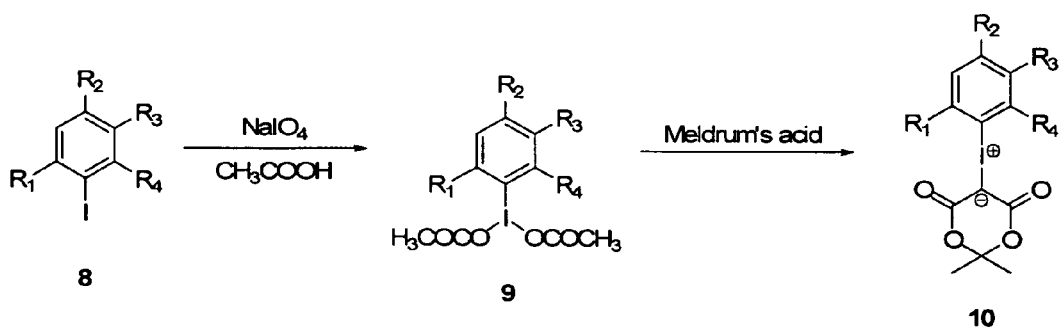
FIG. 2 shows the reaction scheme for the preparation of substituted phenyliodonium ylide derivatives.

Eight substituted phenyliodonium ylides were also similarly synthesized as shown in FIG. 2. The phenyliododiacetoxy derivatives 2 and 9 were prepared by the periodate oxidation of the corresponding iodobenzenes in acetic acid medium as reported in the literature (P. Kazmierczak, L. Skulski and L. Kraszkiewicz, "Syntheses of (Diacetoxyiodo) arenes or Iodylarenes from Iodoarenes, with Sodium Periodate as the Oxidant." *Molecules*, 6, pp 881-891 (2001)). The iodonium ylides 3-5 were synthesized according to the procedure developed by Schank and Lick (K. Schank and C. Lick, "Ozonolytic Fragmentation of Phenyliodonium □-Diketonates: A Convenient Synthesis of Unsolvated vic-Triketones." *Synthesis*, pp 392-395 (1983)) while the compounds 6 and 7 were prepared as reported in the literature (T. Kappe, G. Korbuly, and W. Stadlbauer, "Ylide von Heterocyclen, II. Iodonium- and Pyridinium-Ylide von Malonylheterocyclen." *Chem. Ber.*, 111, pp 3857-3866 (1978)). The molecular weight of the compounds produced was determined using matrix-assisted laser desorption ionization mass spectroscopy (MS-MALDI).

The substituted phenyliodonium ylides 10a-d and 10f-h (FIG. 2) are heretofore unreported in the literature and were newly synthesized for this investigation. Typical experimental procedure used for their synthesis is summarized below:

EXAMPLE 1

2,2-Dimethyl-4,6-dioxo-1,3-dioxan-5-(4-methylphenyl)iodonium ylide (10a)

A solution of 1-(diacetoxyiodo)-4-methylbenzene (9a) (2 mmol) in ethanol (8 mL) was added to a solution of 2,2-dimethyl-1,3-dioxane-4,6-dione (2 mmol) in 10% sodium carbonate in water (6 mL). The mixture was stirred at room temperature for 4 h. The resulting suspension was poured into ice water and extracted with dichloromethane. The organic layer was dried over anhydrous sodium sulfate, filtered and evaporated in a rotary evaporator. The product (10a) was purified by silica gel column flash chromatography using 3% methanol in dichloromethane as the eluent to provide the ylide as a white solid in 87% yield.

$^1$H NMR (CDCl$_3$): ☐ 7.81 (d, 2H, ArH), 7.24 (d, 2H, ArH), 2.43 (s, 3H, CH$_3$), 1.72 (s, 3H, CH$_3$), 1.62 (s, 3H, CH$_3$).

MS (MALDI): Calcd for C$_{13}$H$_{13}$O$_4$I (M$^+$): 359.99. Found: 382.99 (M$^+$+Na).

EXAMPLE 2

2,2-Dimethyl-4,6-dioxo-1,3-dioxan-5-(2,4,6-trimethylphenyl) iodonium ylide (10b)

The synthesis of this ylide (10b) was carried out according to the procedure set forth in Example 1 using the diacetoxy derivative 9b. The product was a white solid obtained in 92% yield.

$^1$H NMR (CDCl$_3$): ☐ 7.26 (d, 2H, ArH), 2.79 (s, 6H, 2 ArCH$_3$), 2.32 (s, 3H, ArCH$_3$), 1.62 (s, 6H, 2 CH$_3$);

MS (MALDI): Calcd for C$_{15}$H$_{17}$O$_4$I (M$^+$): 388.02. Found: 410.67 (M$^+$+Na).

EXAMPLE 3

2,2-Dimethyl-4,6-dioxo-1,3-dioxan-5-(2-methoxyphenyl) iodonium ylide (10c)

This product (10c) was prepared using the procedure set forth above in Example 1 using 1-(diacetoxyiodo)-2-methoxybenzene (9c). A white solid was produced in 68% yield.

$^1$H NMR (CDCl$_3$): ☐ 7.51-7.00 (m, 4H, ArH), 4.01 (s, 3H, OCH$_3$), 1.82 (s, 3H, CH$_3$), 1.58 (s, 3H, CH$_3$).

MS (MALDI): Calcd for C$_{13}$H$_{13}$O$_5$I (M$^+$): 375.98. Found: 398.98 (M$^+$+Na).

EXAMPLE 4

2,2-Dimethyl-4,6-dioxo-1,3-dioxan-5-(3-methoxyphenyl) iodonium ylide (10d)

The diactoxyiodobenzene analog 9d was used for the preparation of the ylide (10d) using the method described above in Example 1. The product was obtained as a white solid in 84% yield.

$^1$H NMR (CDCl$_3$): ☐ 7.43 (m, 2H, ArH), 7.32 (m, 1H, ArH), 7.09 (dd, 1H, ArH), 3.83 (s, 3H, OCH$_3$), 1.72 (s, 6H, 2CH$_3$).

MS (MALDI): Calcd for C$_{13}$H$_{13}$O$_5$I (M$^+$): 375.98. Found: 398.60 (M$^+$+Na).

EXAMPLE 5

2,2-Dimethyl-4,6-dioxo-1,3-dioxan-5-(4-methoxyphenyl) iodonium ylide (10e)

Using the procedure described above starting with 1-(diacetoxyiodo)-4-methoxybenzene (9e), the ylide (10e) was obtained as a white solid in 79% yield.

$^1$H NMR (CDCl$_3$): ☐ 7.50 (s, 2H, ArH), 7.26 (s, 2H, ArH), 3.90 (s, 3H, OCH$_3$), 1.57 (s, 6H, 2CH$_3$)).

MS (MALDI): Calcd for C$_{13}$H$_{13}$O$_5$I (M$^+$): 375.98. Found: 398.98 (M$^+$+Na).

This product (10e) was found to be identical to the same ylide obtained by a previously published procedure (O. Neilands and B. Karele, "Iodonium derivatives of ☐-diketones. XVII. Aryiodonium derivatives of isopropylidene malonate." *J. Org. Chem., USSR* (*Engl. Transl.*), 7, pp 1674-1677 (1971)).

EXAMPLE 6

2,2-Dimethyl-4,6-dioxo-1,3-dioxan-5-(4-bromophenyl)iodonium ylide (10f)

Using the procedure of Example 1 and 1-bromo-4-(diacetoxyiodo)benzene (9f) as a starting material the ylide (10f) was obtained as a pale yellow solid in 69% yield.

$^1$H NMR (CDCl$_3$): ☐ 7.80 (d, 2H, ArH), 7.56 (d, 2H, ArH), 1.73 (s, 6H, 2CH$_3$)).

MS (MALDI): Calcd for C$_{12}$H$_{10}$BrO$_4$I (M$^+$): 423.88. Found: 446.51 (M$^+$+Na).

EXAMPLE 7

2,2-Dimethyl-4,6-dioxo-1,3-dioxan-5-(4-chlorophenyl)iodonium ylide (10g)

Using the procedure given above in Example 1 and diacetoxyiodobenzene derivative 9g the ylide (10g) was produced as a white solid in 71% yield.

$^1$H NMR (CDCl$_3$): ☐ 7.88 (d, 2H, ArH), 7.44 (d, 2H, ArH), 1.73 (s, 6H, CH$_3$), 1.60 (s, 3H, CH$_3$).

MS (MALDI): Calcd for C$_{12}$H$_{10}$ClIO$_4$ (M$^+$): 379.93. Found: 402.55 (M$^+$+Na).

EXAMPLE 8

2,2-Dimethyl-4,6-dioxo-1,3-dioxan-5-(4-nitrophenyl)iodonium ylide (10h)

Using the procedure of Example 1 and starting with the diacetoxy nitrophenyl derivative 9h, the ylide (10h) was obtained in 74% yield.

$^1$H NMR (CDCl$_3$): ☐ 8.28 (d, 2H, ArH), 8.08 (d, 2H, ArH), 1.73 (s, 6H, 2 CH$_3$).

MS (MALDI): Calcd for C$_{12}$H$_{10}$INO$_6$ (M$^+$): 390.96. Found: 413.60 (M$^+$+Na).

Nucleophilic Substitution Reactions with the Phenyliodonium Ylides

The reactivity of phenyliodonium ylides with simple nucleophiles such as halide ions in anhydrous media has not yet been reported in the literature. However, the reactivity of phenyliodonium ylides with Bronsted acids such as HCl and HBr and organic acids such as acetic acid has been demonstrated (O. Neilands and B. Karele, "Iodonium derivatives of ☐-diketones. XVII. Aryiodonium derivatives of isopropylidene malonate." *J. Org. Chem., USSR* (*Engl. Transl.*), 7, pp 1674-1677 (1971); T. Kappe, G. Korbuly, and W. Stadlbauer, "Ylide von Heterocyclen, II. Iodonium-und Pyridinium-Ylide von Malonylheterocyclen." *Chem. Ber.*, 111, pp 3857-3866 (1978); N. S. Habib, "Ylides of Heterocycles. VII. [1]. I-, N-, P- and S-Ylides of Pyrimidones." *J. Heterocyclic Chem.*, 21, pp 385-388 (1984); E. Pongratz and T. Kappe, "Ylide von Heterocyclen. VIII Reaktionen von Iodonium-Yliden mit Sauren." *Monatsh. Chem.*, 115, pp 231-242 (1984)). A typical example of such a reaction is summarized in FIG. 3.

Figure 3:
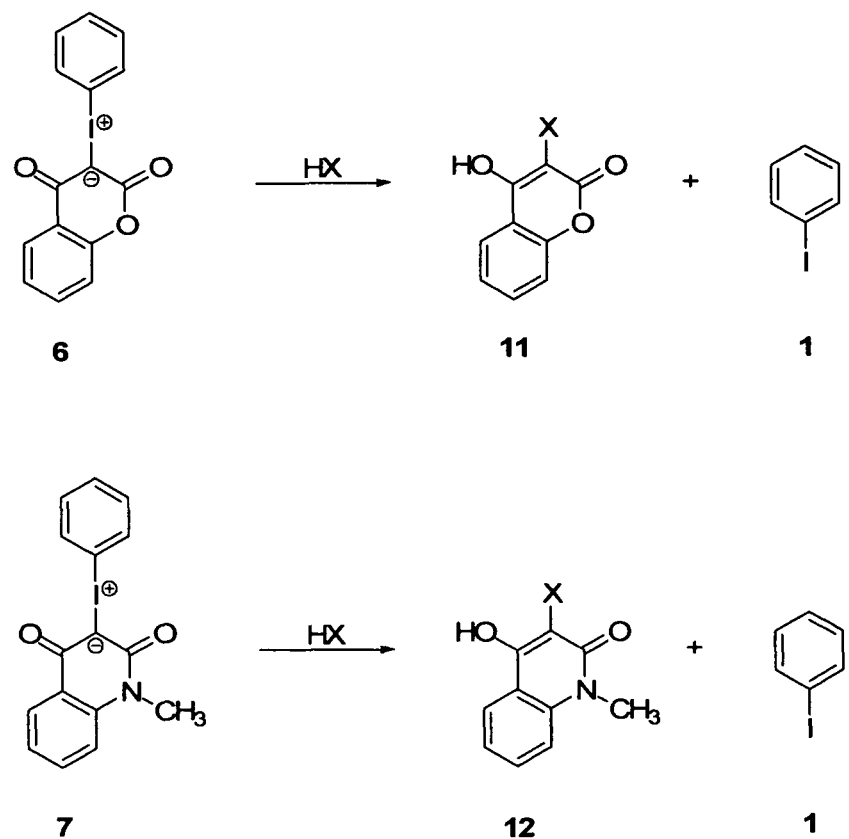
FIG. 3 shows the reaction of two different phenyliodonium ylides with acid.

The reaction of the ylides 6 and 7, for example, with acids like HCl and HBr as well as acetic acid and trifluoroacetic acid first leads to the protonation of one of the keto groups followed by the nucleophilic attack of the conjugate base of the acid on the heterocyclic ring to give the products shown in FIG. 3 identified as 11 and 12 (E. Pongratz and T. Kappe, "Ylide von Heterocyclen. VIII Reaktionen von Iodonium-Yliden mit Sauren." *Monatsh. Chem.*, 115, pp 231-242 (1984)). Thus, iodobenzene (1) acts as a facile leaving group in all these reactions and the nucleophiles (i.e. the conjugate base of the acids) exclusively attack the heterocyclic ring system to form products 11 and 12.

In sharp contrast to the reaction of the iodonium ylides with acids, we found nucleophilic substitution reactions of the ylides 3-7 and 10a-h with fluoride, bromide, chloride etc in polar aprotic solvents led to regiospecific substitution of the nucleophiles on the aromatic ring instead of the dione ring. The nucleophile regiospecically substituted on the aromatic carbon atom that was carrying the positively charged iodine moiety.

Thus, the iododione moieties in 3-7 and 10a-h likely act as the leaving group in this nucleophilic substitution reaction.

Shown herein, for the first time is the reaction of halide ions (fluoride, chloride and bromide) with the iodonium ylides 3-7 and 10a-h in non-aqueous aprotic solvents such as acetonitrile, tetrahydrofuran, dimethylsulfoxide and dimethylacetamide and dimethylformamide. Typical experimental conditions used for the fluoride ion reaction are given below:

EXAMPLE 9

A solution of Kryptofix 2.2.2 (40 □mol) in acetonitrile (1 mL) was added to a solution of KF (25 □mol) in water (0.1 mL). The solvents were evaporated at 120° C. and the residue was dried by azeotropic distillation with acetonitrile (3×1 mL). A solution of the phenyliodonium ylide precursor in dry dimethylformamide (1.0 mL) was added to the dried KF-Kryptofix complex and the reaction vessel was hermetically sealed. The reaction mixture was heated at 130° C. for 15 min. The reaction mixture was cooled to room temperature and processed with a silica gel chromatography column (12×1 cm). The products of the reaction were eluted off the column with diethyl ether (20 mL) and analyzed by GC/MS (30 m×0.25 mm J&W Scientific DB-5MS capillary column; Varian Saturn 2000 mass spectrometer) and by analytical HPLC (Phenomenex Luna C18 column, 5μ particle size, 250×4.6 mm; eluent: methanol/water=75/25; flow rate: 1 mL/min; UV detection at 254 nm).

Figure 4:
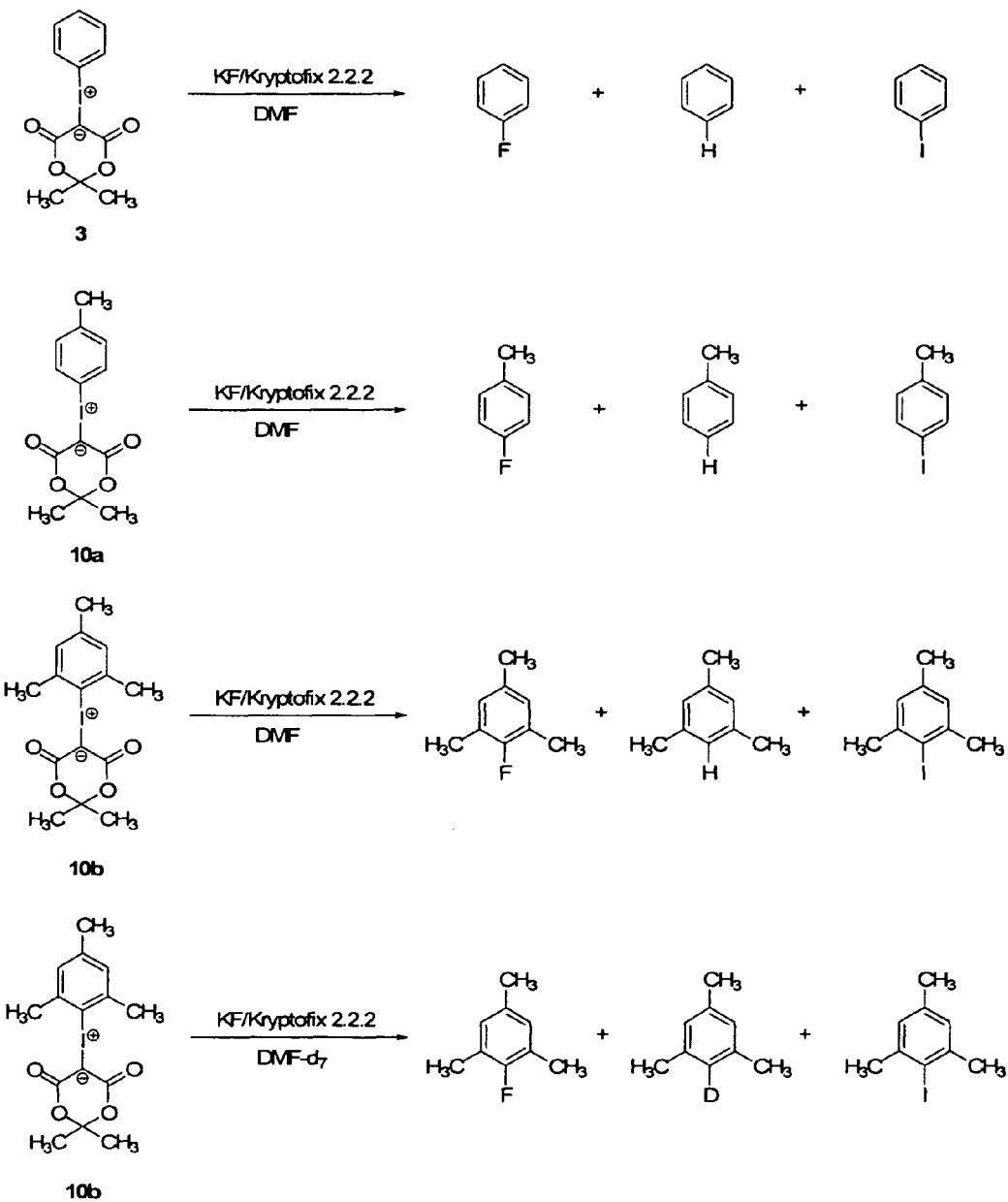
FIG. 4 shows the products formed from the reaction of eight different phenyliodonium ylides with non-radioactive fluoride ion.
Figure 4:
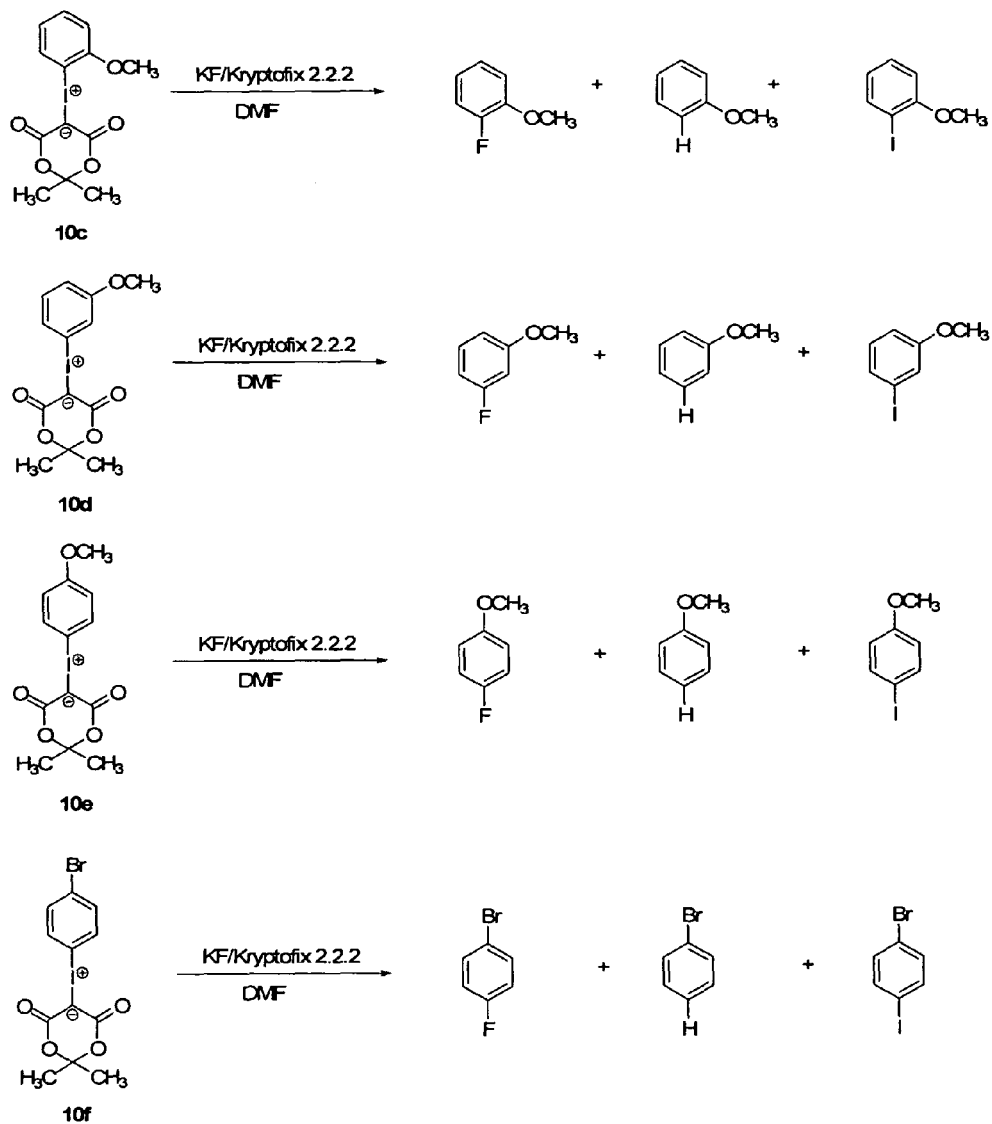

The products observed by GC/MS and analytical HPLC in these reactions are summarized in FIG. 4.

In each of these reactions with the fluoride ion, only three major aromatic products were observed—substitution of the nucleophile on the aromatic ring to yield a fluoroaryl derivative, substitution of hydrogen on the aromatic ring to give the arene and formation of an iodoaryl analog. GC/MS analysis conclusively proved the identity of these products. Analytical HPLC data supported the GC/MS data. The GC/MS analysis showed that the nucleophile (i.e. fluoride) did not substitute on the dione moiety to yield 1-fluoro-2,2-dimethyl-1,3-dioxane-4,6-dione (13) (FIG. 5, Path B) but instead the fluoride substituted regiospecifically on the phenyl ring on the ipso carbon. This observation can be rationalized by the presence of a delocalized negative charge distributed over the dione part of the dioxane ring system which would repel the nucleophile (i.e. fluoride ion) also carrying a negative charge.

Figure 5:
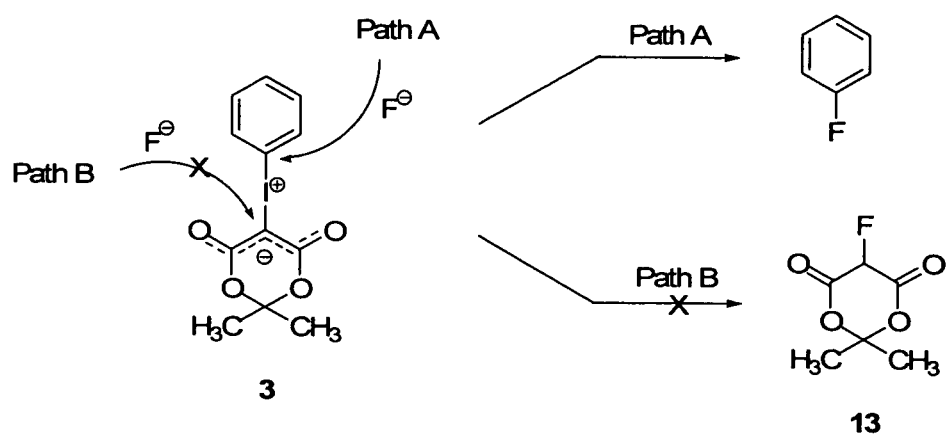
FIG. 5 shows the mechanism of the reaction of phenyliodonium ylide with fluoride ion.

On the other hand, the carbon atom on the aromatic ring carrying the positively charged iodine moiety has an electron deficiency and makes itself a more favorable point for the attack by the nucleophile to yield the fluoroaryl derivative (FIG. 5, Path A). Substitution of hydrogen on the aromatic ring to give the hydrocarbon derivatives (i.e. benzene, toluene, mesitylene, anisole etc) strongly indicate involvement of a competing radical pathway for this nucleophilic substitution reaction and abstraction of hydrogen from the solvent. Such a radical pathway has previously been observed in the nucleophilic reaction of fluoride with the closely related iodonium salts (M. Van Der Puy, "Conversion of Diaryiodonium Salts to Aryl Fluorides." *J. Flourine Chem.* 21, pp 385-392 (1982)). Thus, when the trimethyl substituted iodonium ylide (10b) reaction was conducted in a deuterated solvent (e.g. DMF-$d_7$) GC/MS analysis showed the presence of deuteromesitylene (FIG. 4) in the product mixture indicating a radical channel competing with the nucleophilic substitution reaction.

EXAMPLE 10

Conditions for a radiolabeling reaction are as follows: No-carrier-added [F-18]fluoride ion was produced by proton bombardment of [O-18]water in a cyclotron target body. The only fluorine moiety produced is the [F-18]ion. The aqueous [F-18]fluoride ion was treated with 1.0 mg of potassium carbonate and 10 mg of Kryptofix 2.2.2.® compound to form an aqueous solution. Kryptofix 2.2.2® compound is one example of a family of synthetic bi- and polycyclic multidentate ligands capable of encapsulating a variety of cations, referred to generically as cryptands. Kryptofix 222® is 4,7,13,16,21,24-Hexaoxa-1,10-diazabicyclo[8.8.8]-hexacosane ($C_{18}H_{36}N_2O_6$) with the following chemical structure:

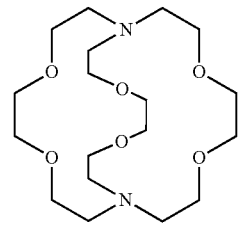 [SMILES: C1COCCN2CCOCCOCCN(CCO1)CCOCCOCC2]

The aqueous solution was evaporated at 120° C. and the residue was further dried by azeotropic distillation with acetonitrile. Alternative encapsulating compounds can be used in place of Kryptofix 2.2.2®. For example, dry no-carrier-added $Cs^{18}F$ or tetraalkylammonium [F-18]fluoride can be used in the place of $K^{18}F$-Kryptofix complex for the nucleophilic substitution reaction described above. Dry no-carrier-added $Cs^{18}F$ is prepared by treating $Cs_2CO_3$ (1 mg) with [F-18] fluoride ion prepared by the proton irradiation of [O-18] water and evaporating the water as an azeotrope with acetonitrile. Tetraalkylammonium [F-18] fluoride (examples of preferred alkyl groups are methyl, ethyl, propyl, butyl, benzyl) is similarly prepared from the corresponding bicarbonate salt.

A phenyliodonium ylide derivative (about 7 to 10 mg) was dissolved in dry DMF (1 mL) and added to the dried potassium [F-18]fluoride/Kryptofix complex or $Cs^{18}F$ or [F-18] tetraalkylammonium fluoride as prepared above. The reaction vessel was then hermetically sealed with a glass or silicone stopper and heated to a temperature between 110°-130° C. for 10-15 min. The reaction mixture was cooled to room temperature and transferred to a silica gel chromatography column (12×1 cm) where it was equilibrated with diethyl ether. The column, upon elution with 10-15 mL of ether, provided the [F-18]fluorobenzene derivatives as evidenced by radioHPLC and radioTLC analyses. Alternatively, the reaction mixture can be processed using a Waters Corporation C-18 Sep-Pak® instead of the silica gel column. If the C-18

Sep-Pak® is used, the reaction mixture was diluted with 10 mL of water and passed through a C-18 Sep-Pak® pre-equilibrated with methanol (5 mL) followed by water (10 mL). The Sep-Pak® was flushed with water (10 mL) and the product was eluted out with 2 mL of methanol. The crude product recovered by either method was found to ≥95% radiochemically pure. However, ≥99% radiochemically and chemically pure product was obtained by semi-preparative HPLC purification of the crude reaction mixture using silica or C-18 HPLC columns.

Table 1 lists various phenyliodonium ylide precursors and the F-18 labeled aryl derivatives described above obtained therefrom using this method along with the radiochemical yields.

TABLE 1

Nucleophilic Fluorination of Phenyl Iodonium Ylides with No-Carrier-Added [$^{18}$F]Fluoride Ion

| Iodonium ylide precursor | Product | Radiochemical yield (%) |
|---|---|---|
| 3 | | 61.6 |
| 4 | | 26.8 |
| 5 | | 63.4 |
| 6 | | 63.7 |
| 7 | | 34.4 |

The iodonium ylides 10a-h were also successfully reacted with no-carrier-added [F-18]fluoride ion as described in the above procedure and the radiochemical yields obtained for various [F-18]fluoroaryl derivatives are listed in Table 2.

TABLE 2

Nucleophilic Fluorination of Substituted Phenyl Iodonium Ylides with No-Carrier-Added [$^{18}$F]Fluoride Ion

| Phenyl iodonium ylide | Product | Radiochemical yield (%) |
|---|---|---|
| 3 | | 61.6 |

TABLE 2-continued

Nucleophilic Fluorination of Substituted Phenyl Iodonium Ylides with No-Carrier-Added [$^{18}$F]Fluoride Ion

| Phenyl iodonium ylide | Product | Radiochemical yield (%) |
|---|---|---|
| 10a (4-methylphenyl iodonium ylide) | 4-[$^{18}$F]fluorotoluene | 58.5 |
| 10b (2,4,6-trimethylphenyl iodonium ylide) | 2,4,6-trimethyl-[$^{18}$F]fluorobenzene | 62.7 |
| 10c (2-methoxyphenyl iodonium ylide) | 2-methoxy-[$^{18}$F]fluorobenzene | 75.6 |
| 10d (3-methoxyphenyl iodonium ylide) | 3-methoxy-[$^{18}$F]fluorobenzene | 19.0 |
| 10e (4-methoxyphenyl iodonium ylide) | 4-methoxy-[$^{18}$F]fluorobenzene | 32.3 |
| 10f (4-bromophenyl iodonium ylide) | 4-bromo-[$^{18}$F]fluorobenzene | 73.0 |
| 10g (4-chlorophenyl iodonium ylide) | 4-chloro-[$^{18}$F]fluorobenzene | 72.9 |

TABLE 2-continued

Nucleophilic Fluorination of Substituted Phenyl Iodonium Ylides with No-Carrier-Added [$^{18}$F]Fluoride Ion

| Phenyl iodonium ylide | Product | Radiochemical yield (%) |
|---|---|---|
| 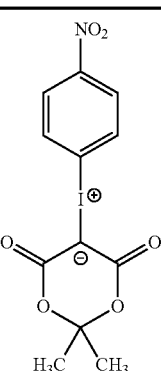 10h | 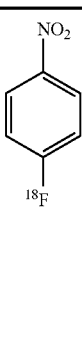 | 87.3 |

Figure 6:
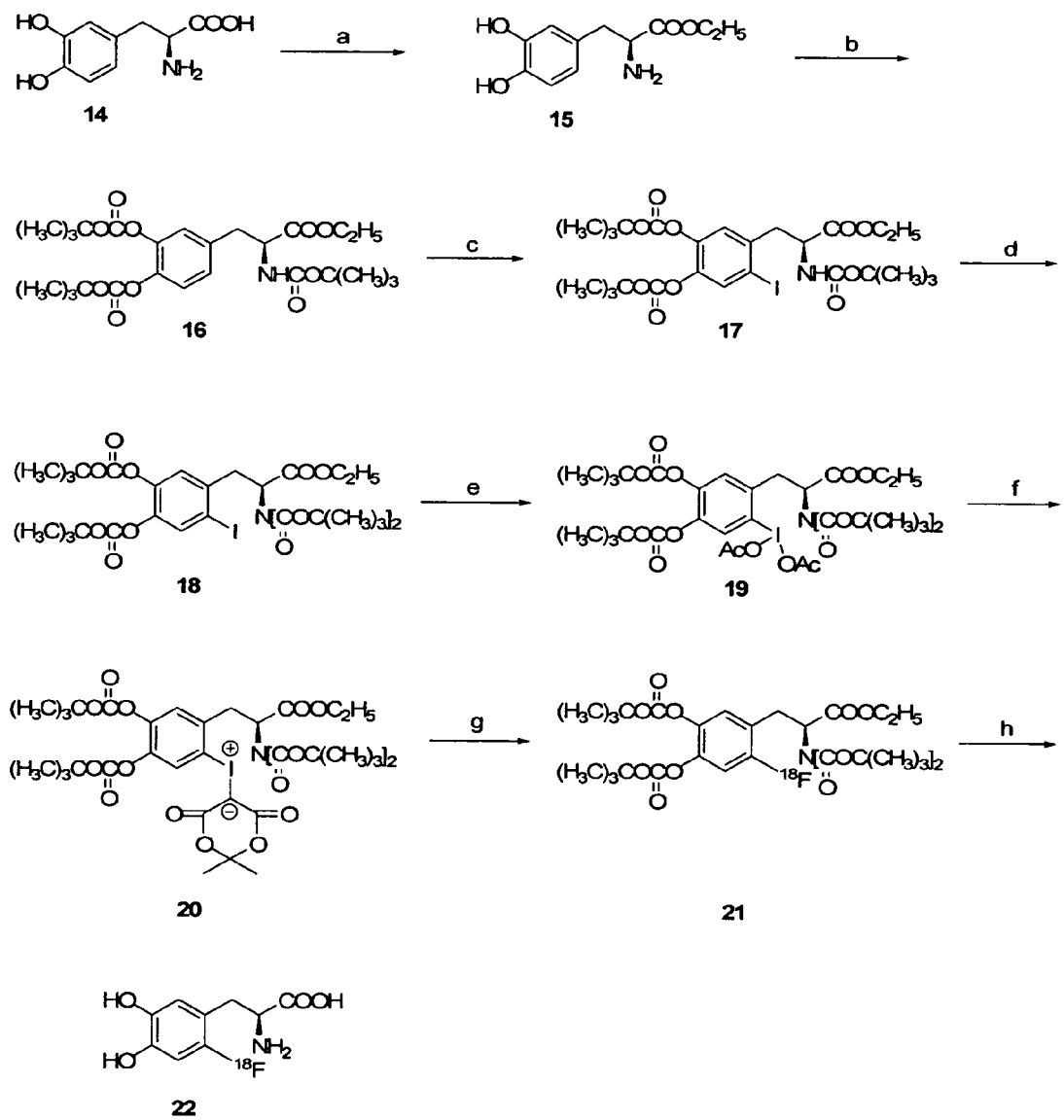
FIG. 6 shows the reaction scheme for the synthesis of 6-[F-18]fluoro-L-dopa.

The versatility of the fluorination reaction described herein is further demonstrated in Example 11 and FIG. 6 wherein 6-[F-18]fluoro-L-dopa (21) was synthesized. The F-18 labeled amino acid (L-dopa) 21 is a very useful PET imaging agent for mapping dopamine related brain disorders as well as brain tumors and is the PET biomarker of choice for the diagnosis of Parkinson's disease.

EXAMPLE 11

The synthesis of the intermediate compounds and the preparation of the [F-18] fluoro-L-dopa is as follows:

a) 3,4-Dihydroxy-L-phenylalanine ethyl ester (15)

Standard Fisher esterfication of L-dopa (14) (0.13 mol) in anhydrous ethanol (500 mL) with dry HCl gas provided the ester 15 in quantitative yield.

b) N-(tert-butoxycarbonyl)-3,4-di(tert-butoxycarbonyloxy)-L-phenylalanine ethyl ester (16)

The ester 15 (38 mmol) was dissolved in dry DMF (60 mL) under argon and triethylamine (460 mmol) was added under stirring. A solution of di-tert-butyl dicarbonate (153 mmol) in dry DMF (40 mL) was then added drop-wise and the reaction mixture was stirred overnight at room temperature. The solution was then diluted with ethylacetate (60 mL) and washed with brine (2×100 mL) followed by water (3×100 mL). The organic layer was dried over anhydrous sodium sulfate, filtered and evaporated to produce the ester 16 as a white foam in 97% yield.

($^1$H NMR (CDCl$_3$): □ 7.18 (d, 1H, ArH), 7.03 (s, 1H, ArH), 7.00 (d, 1H, ArH), 5.03 (broad d, 1H, NH), 4.54 (q, 1H), 4.19-4.11 (m, 2H), 3.09 (m, 2H), 1.54 (s, 18H), 1.43 (s, 9H), 1.22 (t, 3H);

($^{13}$C NMR (CDCl$_3$): □ 171.50, 155.08, 150.71, 150.60, 142.29, 141.45, 134.80, 127.19, 124.00, 122.97, 116.41, 83.74, 79.98, 61.54, 60.39, 54.24, 37.55, 21.05, 14.19, 14.08;

MS (MALDI): Calcd for C$_{26}$H$_{39}$NO$_{10}$ (M$^+$): 525.26. Found: 548.07 (M$^+$+Na)).

c) N-(tert-butoxycarbonyl)-3,4-di(tert-butoxycarbonyloxy)-6-iodo-L-phenylalanine ethyl ester (17)

Iodine (7.4 mmol) and bis(trifluoroacetoxy)iodobenzene (8.16 mmol) were added to a solution of the tri-boc protected dopa ester analog 16 (5.7 mmol) in anhydrous dichloromethane (60 mL) under argon. The reaction mixture was stirred at room temperature for 40 min and then quenched with a saturated solution of sodium thiosulfate. The organic layer was washed with water (3×10 mL), dried with anhydrous sodium sulfate, filtered and evaporated in a rotary evaporator. The product was purified by silica gel column chromatography using 15-20% ethyl acetate in hexane as the mobile phase to give the iodo analog 17 as white foam in 77% yield.

($^1$H NMR (CDCl$_3$): □ 7.74 (s, 1H, ArH), 7.14 (s, 1H, ArH), 5.08 (broad d, 1H, NH), 4.59 (q, 1H), 4.22-4.12 (m, 2H), 3.20 (m, 2H), 1.55 (s, 18H), 1.42 (s, 9H), 1.22 (t, 3H);

$^{13}$C NMR (CDCl$_3$): □ 171.61, 154.97, 150.25, 150.19, 142.57, 141.50, 138.13, 133.50, 124.24, 95.47, 84.19, 84.07, 80.03, 61.69, 60.40, 53.47, 42.56, 28.27, 27.59, 21.07, 14.03;

MS (MALDI): Calcd for C$_{26}$H$_{38}$NO$_{10}$I (M$^+$): 651.15. Found: 674.00 (M$^+$+Na).

d) N-di(tert-butoxycarbonyl)-3,4-di(tert-butoxycarbonyloxy)-6-iodo-L-phenylalanine ethyl ester (18)

The iodo analog 17 (0.76 mmol) was dissolved in dry THF (5 mL) under argon and 4-(dimethylamino)pyridine (3.8 mmol) and di-tert-butyldicarbonate (2.85 mmol) were added. The reaction mixture was stirred at room temperature overnight. The resulting yellow solution was diluted with ethyl acetate and washed with water (3×30 mL). The ethyl acetate layer was dried with anhydrous sodium sulfate, filtered and evaporated to produce a semi-solid residue. This crude product upon purification by flash chromatography over silica gel with 15-20% ethyl acetate in hexane as eluent gave the tetra boc derivative 18 in 74% yield as white foam.

($^1$H NMR (CDCl$_3$): □ 7.68 (s, 1H, ArH), 7.06 (s, 1H, ArH), 5.24 (q, 1H), 4.24-4.08 (m, 2H), 3.20 (m, 2H), 1.52 (s, 18H), 1.38 (s, 18H), 1.20 (t, 3H);

$^{13}$C NMR (CDCl$_3$): □ 169.87, 151.76, 150.16, 150.11, 142.48, 141.33, 139.13, 133.24, 124.86, 95.41, 84.07, 83.87, 83.18, 61.53, 57.39, 40.15, 27.86, 27.57, 14.16;

MS (MALDI): Calcd for C$_{31}$H$_{46}$NO$_{12}$I (M$^+$): 751.21. Found: 774.07 (M$^+$+Na)).

e) N-di-(tert-butoxycarbonyl)-3,4-di(tert-butoxycarbonyloxy)-6-(diacetoxy)iodo-L-phenylalanine ethyl ester (19)

The dimethyldioxirane (DMDO) reagent was prepared as reported in the literature (R. W. Murray and M. Singh, "Synthesis of epoxides using dimethyldioxirane: trans-stilbene oxide." Org. Syn., 74, pp 91-96 (1998)). Acetone (40 mL) was added to a solution of sodium bicarbonate (12.0 g) in water (50 mL). The white suspension formed was cooled in an ice bath to 0° C. and solid oxone (24.0 g) was added over a period of 10-15 min with vigorous stirring. The mixture was stirred at 0° C. for an additional period of 5 min and then distilled at room temperature for 45-60 min under vacuum (100 torr). A pale yellow distillate of DMDO (~30 mL) in acetone, collected in a flask cooled in a −78° C. bath, was dried with anhydrous sodium sulfate and filtered. The pale yellow filtrate containing DMDO was used immediately in the next step.

The DMDO reagent was added drop-wise to an ice cold solution of the tetraboc iodo derivative 18 (0.27 mmol) in acetone-acetic acid (4:1) (2.0 mL) and the solution was stirred at 0° C. in an ice bath under argon for 1 h. The ice bath was then removed and the reaction mixture was stirred at room temperature for 3 h. The solvents were pumped off under high vacuum to leave the iodo-diacetoxy dopa analog 19 as white solid in 91% yield. The product was used in the next step without further purification.

($^1$H NMR (CDCl$_3$): ☐ 8.11 (s, 1H, ArH), 7.45 (s, 1H, ArH), 5.24 (q, 1H), 4.25-4.15 (m, 2H), 3.66 (m, 2H), 2.09 (s, 6H), 1.54 (s, 18H), 1.41 (s, 18H), 1.26 (t, 3H);

$^{13}$C NMR (CDCl$_3$): .. 176.87, 176.67, 169.57, 151.71, 149.91, 149.84, 149.76, 145.31, 141.88, 139.64, 132.41, 125.22, 121.60, 84.62, 84.57, 83.56, 61.81, 59.14, 38.79, 27.99, 27.87, 27.57, 20.74, 20.33, 14.12;

MS (MALDI): Calcd for $C_{35}H_{52}NO_{16}I$ (M$^+$): 869.23. Found: 892.00 (M$^+$+Na)).

f) 2,2-Dimethyl-4,6-dioxo-1,3-dioxan-5-[N-di(tert-butoxycarbonyl)-3,4-di-(tert-butoxycarbonyloxy)-L-phenylalanine ethyl ester-6-iodonium]ylide (20)

2,2-dimethyl-4,6-dioxo-1,3-dioxane (0.27 mmol) was added under argon to a solution of the iododiacetoxy dopa analog 19 (0.27 mmol) in anhydrous dichloromethane (6 mL) and the solution was stirred at room temperature overnight. The solvent was then evaporated and the product purified by flash chromatography on silica gel using 60-70% ethyl acetate in hexane as eluent to give the iodonium ylide 20 in 68% yield.

($^1$H NMR (CDCl$_3$): ☐ 7.99 (s, 1H, ArH), 7.39 (s, 1H, ArH), 5.31 (q, 1H), 4.25-4.18 (m, 2H), 3.93-3.29 (m, 2H), 1.68 (s, 6H), 1.56 (s, 18H), 1.53 (s, 18H), 1.26 (t, 3H);

$^{13}$C NMR (CDCl$_3$): ☐ 170.36, 164.02, 151.76, 149.73, 149.59, 145.72, 145.42, 138.05, 129.80, 125.30, 118.04, 104.34, 84.69, 84.60, 84.25, 62.18, 59.57, 59.07, 39.47, 27.96, 27.81, 27.49, 25.96, 13.96;

MS (MALDI): Calcd for $C_{37}H_{53}NO_{16}I$ (M$^+$): 894.24. Found: 916.07 (M$^+$+Na)).

g) 6-[F-18]fluoro-L-dopa (21)

No-carrier-added [F-18]fluoride ion was produced by proton bombardment of [O-18]water in a cyclotron. The aqueous [F-18]fluoride ion was treated with 1.0 mg of potassium carbonate and 10 mg of Kryptofix 2.2.2. The aqueous solution was evaporated at 120° C. and the residue was dried by azeotropic distillation with acetonitrile. The iodonium ylide 20 (15-25 mg) was dissolved in dry DMF (1.0 mL) and added to the dried potassium [F-18]fluoride/Kryptofix complex as prepared above. The reaction mixture was heated at 130° C. for 15 min. The reaction mixture was cooled to room temperature and was diluted with 3 mL of ice water and passed through a C-18 Sep-Pak pre-equilibrated with methanol (5 mL) followed by water (10 mL). The Sep-Pak was flushed with water (10 mL) and the F-18 labeled intermediate product 21 was eluted out with 3 mL of chloroform. The chloroform was evaporated with a stream of nitrogen gas at 125° C.

h) Purified 6-[F-18] fluoro-L-dopa (22)

The residue after evaporation of the chloroform was subjected to acid hydrolysis with 37% HCl at 125° C. for 15 min. The acidic solution was partially neutralized with 0.5 mL of 3M sodium hydroxide in water. Analytical HPLC analysis (Waters ☐Bondapak C-18 column; 97:3=0.1% acetic acid in water:methanol; flow rate: 1 mL/min) of this product indicated the production of radiochemically pure 6-[F-18]fluoro-L-dopa (22) in amounts usable for human PET studies.

Figure 7:
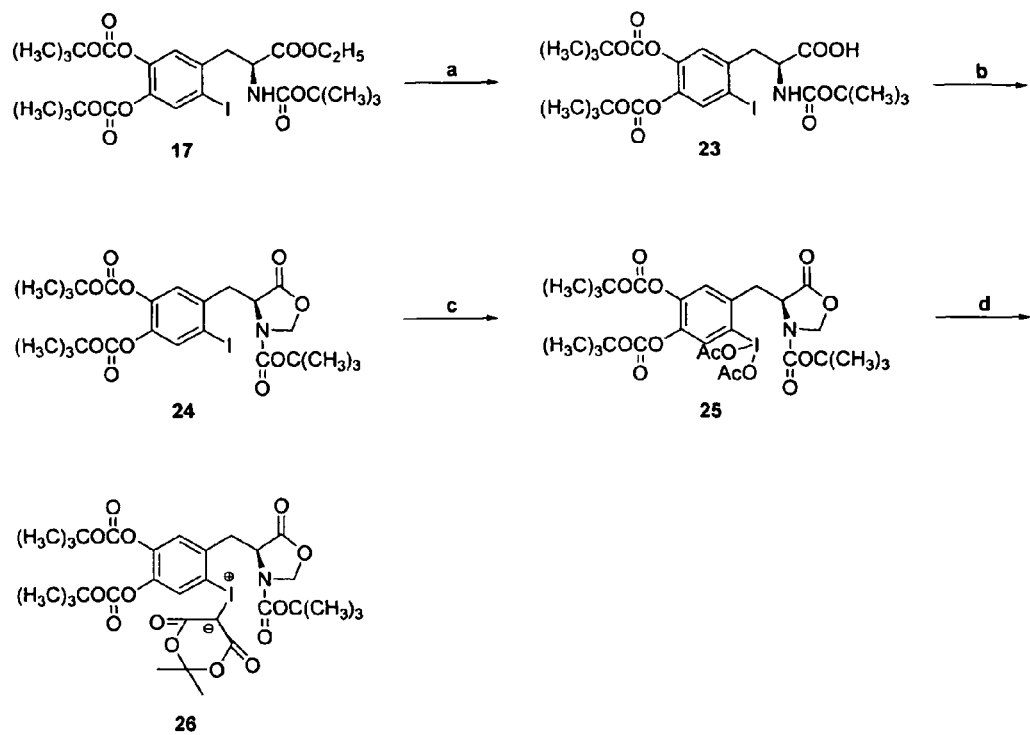
FIG. 7 shows the reaction scheme for the synthesis of the oxazolidinone based iodonium ylide precursor for the preparation of 6-[F-18]fluoro-L-dopa.
Figure 8:
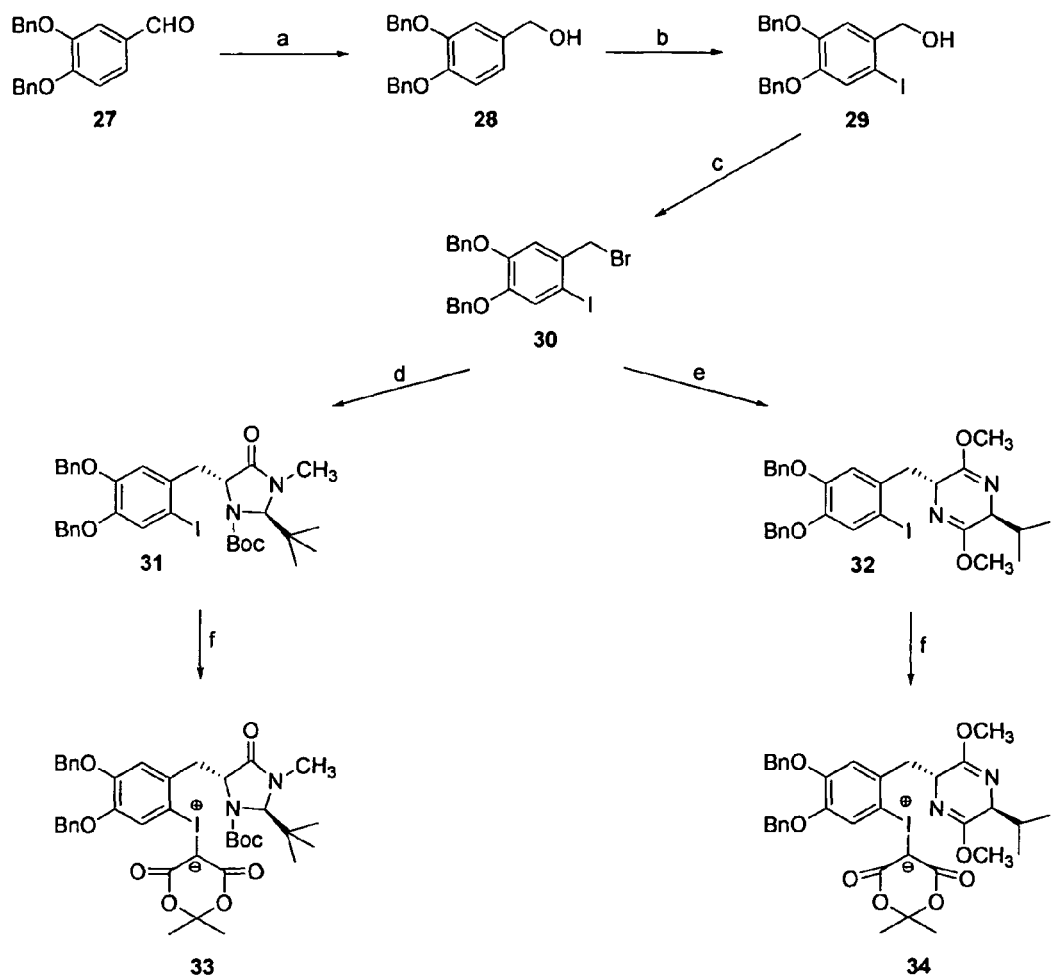
FIG. 8 shows the reaction scheme for the synthesis of the oxoimidazolidine and pyrazine based iodonium ylide precursors for the preparation of 6-[F-18]fluoro-L-dopa

The synthesis of specific examples of iodonium ylide precursors of amino acids are shown in FIGS. 7 and 8. These precursors demonstrate the usefulness and the protein nature of the nucleophilic F-18 fluorination process shown herein. Examples 12 and 13 describe the details pertaining to the preparation of specific amino acid based iodonium ylide precursors.

In general iodonium ylide analogs having the formula:

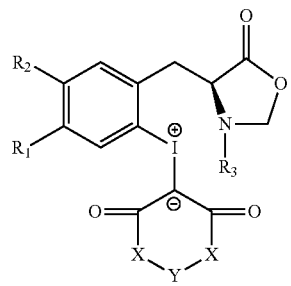

wherein:

$R_1=R_2=R_3=OCOOC(CH_3)_3$, or $R_1=R_2=OCOOC(CH_3)_3$, OCH$_3$ and $R_3=COCH_3$, COOCH$_2$Ph, or $R_1=H$; $R_2=OCOOC(CH_3)_3$, OCH$_3$ and $R_3=COCH_3$, COOCH$_2$Ph, or $R_1=OCOOC(CH_3)_3$, OCH$_3$; $R_2=H$ and $R_3=COCH_3$, COOCH$_2$Ph, and $X=CH_2$, O, S, NCH$_3$, NCH$_2$Ph and $Y=CH_2$, C(CH$_3$)$_2$, =O can be prepared by hydrolyzing an ester group in protected L-iododopa or L-iodotyrosine analogs, cyclizing an amino acid group therein, oxidizing an iodo group therein into a diacetoxyiodo moiety and subsequently reacting the resultant compound with a cyclo 1,3-dicarbonyl derivative.

The resultant iodo compounds can then be converted to F-18 chiral analogs as follows:

F-18 chiral analogs having the formula:

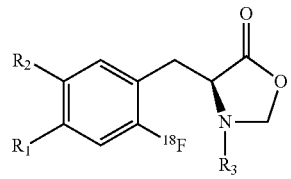

can be prepared by the nucleophilic substitution of a iodonium ylide group in a chiral derivative having the formula

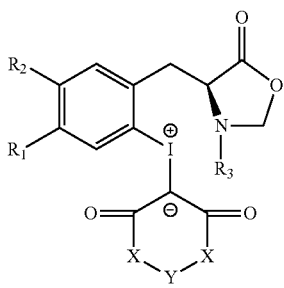

wherein:
 $R_1=R_2=R_3=OCOOC(CH_3)_3$, or
 $R_1=R_2=OCOOC(CH_3)_3$, $OCH_3$ and $R_3=COCH_3$, $COOCH_2Ph$, or
 $R_1=H$; $R_2=OCOOC(CH_3)_3$, $OCH_3$ and $R_3=COCH_3$, $COOCH_2Ph$ or
 $R_1=OCOOC(CH_3)_3$, $OCH_3$; $R_2=H$ and $R_3=COCH_3$, $COOCH_2Ph$, and
 $X=CH_2$, O, S, $NCH_3$, $NCH_2Ph$ and
 $Y=CH_2$, $C(CH_3)_2$, =O by the nucleophilic substitution, using dry heating or microwave heating, of the iodonium ylide group in said chiral derivative, providing a dry, anhydrous no-carrier-added F-18 fluoride ion, said F-18 fluoride ion being derived from a [F-18]KF/Kryptofix complex, [F-18]CsF or quaternary ammonium fluoride, the quaternary ammonium groups being selected from tetramethyl, tetraethyl, tetra n-butyl, and tetrabenzyl.

F-18 labeled L-amino acids or D-amino acids having the formula:

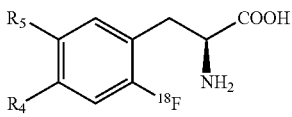

wherein:
 $R_4=R_5=OH$
 $R_4=H$; $R_5=OH$
 $R_4=OH$; $R_5=H$ can be prepared by acid hydrolysis of protected F-18 labeled D-chiral or L-chiral analogs respectively having the formula:

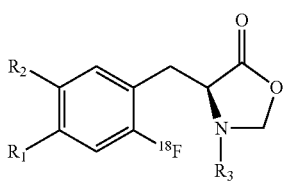

using mineral acids, such as HCl, HBr or HI, under dry heating or microwave heating conditions wherein
 $R_1=R_2=R_3=OCOOC(CH_3)_3$, or
 $R_1=R_2=OCOOC(CH_3)_3$, $OCH_3$ and $R_3=COCH_3$, $COOCH_2Ph$, or
 $R_1=H$; $R_2=OCOOC(CH_3)_3$, $OCH_3$ and $R_3=COCH_3$, $COOCH_2Ph$ or
 $R_1=OCOOC(CH_3)_3$, $OCH_3$, $R_2=H$ and $R_3=COCH_3$, $COOCH_2Ph$.

Example 12 describes a procedure for preparing a specific compound in the manner described above

EXAMPLE 12

FIG. 7 shows of forst embodiment of the reaction scheme for the synthesis of the oxazolidinone based iodonium ylide precursor.

a) N-(tert-butoxycarbonyl)-3,4-di(tert-butoxycarbonyloxy)-6-iodo-L-phenylalanine (23)

The iodo derivative 17 (3.5 mmol) (prepared as shown in FIG. 6) was dissolved in 40 mL of THF and cooled in an ice bath (0° C.) and a solution of lithium hydroxide (7.0 mmol) in 12 mL of water was added dropwise under argon. The resulting mixture was stirred at 0° C. for 4 h and then 2 h at room temperature. The reaction mixture was then neutralized with acetic acid to pH 5 and extracted with ethyl acetate. The organic phase was dried using $Na_2SO_4$, filtered and evaporated to dryness to provide an oil which was purified by silical gel column chromatography resulting in N-(tert-butoxycarbonyl)-3,4-di(tert-butoxycarbonyloxy)-6-iodo-L-phenylalanine (23).

$^1$H NMR ($CDCl_3$): δ 7.76 (s, 1H, ArH), 7.18 (s, 1H, ArH), 5.07 (d, 1H, NH), 4.60 (m, 1H), 3.12-3.40 (m, 2H,), 1.51 (s, 18H), 1.42 (s, 9H).
MS (MALDI): Calcd for $C_{24}H_{34}INO_{10}$ ($M^+$): 623.12. Found: 645.93 ($M^+$+Na).

b) N-(tert-butoxycarbonyl)-1,3-oxazolidin-5-one derivative (24)

A mixture of the iodo amino acid 23 (0.86 mmol), camphorsulfonic acid (0.17 mmol), paraformaldehyde (1.29 mmol) and benzene (10 mL) was refluxed for 2 h. The mixture was diluted with ethyl acetate and was washed with 5% aqueous sodium bicarbonate solution. The organic phase was dried with anhydrous sodium sulfate, filtered and purified by silica gel column chromatography using 40% EtOAc/Hexane mixture as eluent to obtain pure oxazolidinone product 24 (N-(tert-butoxycarbonyl)-1,3-oxazolidin-5-one derivative) as an oil in 35% yield.

$^1$H NMR ($CDCl_3$): δ 7.75 (s, 1H, ArH), 7.15 (s, 1H, ArH), 5.07 (d, 1H, NH), 4.60 (m, 1H), 3.12-3.40 (m, 2H), 1.51 (s, 18H), 1.42 (s, 9H).
MS (MALDI): Calcd for $C_{25}H_{34}INO_{10}$ ($M^+$): 635.12. Found: 657.80 ($M^+$+Na).

c) Diacetoxyiodo N-(tert-butoxycarbonyl)-1,3-oxazolidin-5-one derivative (25)

Thirty one mL of the DMDO reagent in acetone, prepared as described above, was added drop-wise to an ice cold solution of the iodo oxazolidin-5-one derivative 24 (0.31 mmol) in acetone-acetic acid (4:1) (2.0 mL) and the solution was stirred at 0° C. in an ice bath under argon for 2 h. The ice bath was then removed and the reaction mixture was stirred at room temperature for 3 h. The solvents were evaporated under high vacuum to leave a diacetoxyiodo oxazolidinone analog 25 (Diacetoxyiodo N-(tert-butoxycarbonyl)-1,3-oxazolidin-5-one derivative) as an oil in 96.5% yield.

$^1$H NMR ($CDCl_3$): δ 8.15 (s, 1H, ArH), 7.48 (s, 1H, ArH), 4.98 (d, 1H, NH), 4.60 (m, 1H), 3.15-3.50 (m, 2H), 2.01 (s, 18H), 1.47 (s, 9H).
MS (MALDI): Calcd for $C_{29}H_{40}INO_{14}$ ($M^+$): 753.15. Found: 775.93 ($M^+$+Na).

The product was used in the next step without further purification.

d) 2,2-Dimethyl-4,6-dioxo-1,3-dioxane iodonium ylide derivative 26

2,2-dimethyl-4,6-dioxo-1,3-dioxane (0.30 mmol) was added under argon to a solution of the iododiacetoxy oxazolidinone analog 25 (0.30 mmol) in anhydrous dichloromethane (6 mL) and the solution was stirred at room temperature overnight. The solvent was then evaporated and the product purified by flash chromatography on silica gel using 60-70% ethyl acetate in hexane as eluent to give the iodonium ylide 2,2-Dimethyl-4,6-dioxo-1,3-dioxane iodonium ylide derivative 26 as a white solid in 16% yield.

$^1$H NMR (CDCl$_3$): δ 8.06 (s, 1H, ArH), 7.29 (s, 1H, ArH), 5.02 (d, 1H, NH), 4.57 (m, 1H), 3.63-3.77 (m, 2H), 1.67 (s, 6H), 1.56 (s, 18H), 1.53 (s, 9H).

MS (MALDI): Calcd for $C_{31}H_{40}INO_{14}$ (M$^+$): 777.15. Found: 799.73 (M$^+$+Na).

In general, iodonium ylide derivatives having the formula

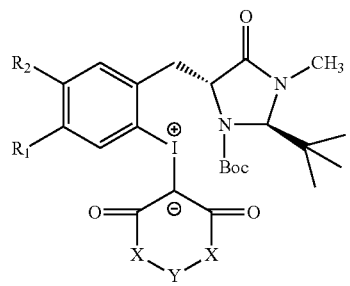

wherein:
$R_1$=$R_2$=OCH$_2$Ph, OCOOC(CH$_3$)$_3$, OCH$_3$, or
R1=H and $R_2$=OCH$_2$Ph, OCOOC(CH$_3$)$_3$, OCH$_3$, or
$R_1$=OCH$_2$Ph, OCOOC(CH$_3$)$_3$, OCH$_3$ and $R_2$=H and
X=CH$_2$, O, S, NCH$_3$, NCH$_2$Ph
Y=CH$_2$, C(CH$_3$)$_2$, =O can be prepared by reacting:

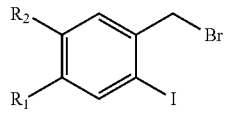

with a chiral oxoimidazolidine auxiliary to produce a protected chiral amino acid derivatives, reacting the resultant compound with dimethyldioxirane in the presence of acetic acid to produce a diacetoxyiodo analog and subsequently reacting the diacetoxyiodo analog with a cyclo 1,3-dicarbonyl derivative.

Additionally, iodonium ylides having the formula

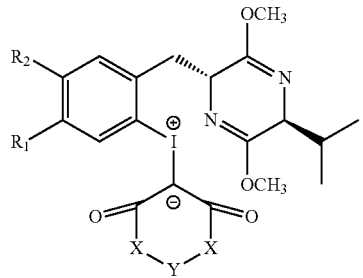

can be prepared by reacting

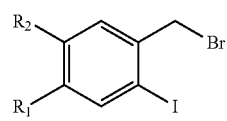

with a chiral pyrazine auxiliary to produce protected chiral amino acid derivatives, reacting the resultant compound with dimethyldioxirane in the presence of acetic acid to produce a diacetoxyiodo analog and subsequently reacting the diacetoxyiodo analog with the cyclo 1,3-dicarbonyl derivatives wherein:
$R_1$=$R_2$=OCH$_2$Ph, OCOOC(CH$_3$)$_3$, OCH$_3$ or
R1=H; $R_2$=OCH$_2$Ph, OCOOC(CH$_3$)$_3$, OCH$_3$ or
$R_1$=OCH$_2$Ph, OCOOC(CH$_3$)$_3$, OCH$_3$; $R_2$=H and
X=CH$_2$, O, S, NCH$_3$, NCH$_2$Ph
Y=CH$_2$, C(CH$_3$)$_2$, =O

The resultant iodo compounds can then be converted to F-18 chiral analogs having the formula

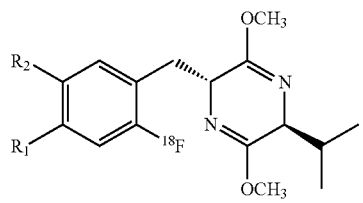

by the nucleophilic substitution of the iodonium ylide group in a chiral analog having the formula:

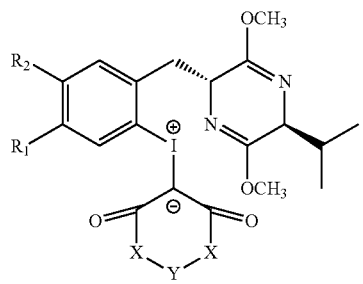

by using dry, anhydrous no-carrier-added F-18 fluoride ion and dry heating or microwave heating where the F-18 fluoride ion is derived from [F-18]KF/Kryptofix complex, [F-18]CsF or quaternary ammonium fluoride, the quaternary ammonium groups selected from tetramethyl, tetraethyl, tetra n-butyl, and tetrabenzyl wherein $R_1=R_2=OCH_2Ph$, $OCOOC(CH_3)_3$, $OCH_3$ or
R1=H; $R_2=OCH_2Ph$, $OCOOC(CH_3)_3$, $OCH_3$ or
$R_1=OCH_2Ph$, $OCOOC(CH_3)_3$, $OCH_3$; $R_2=H$ and
$X=CH_2$, O, S, $NCH_3$, $NCH_2Ph$ and
$Y=CH_2$, $C(CH_3)_2$, =O Additionally, resultant iodo compounds can be converted to F-18 labeled L-amino acids having the formula

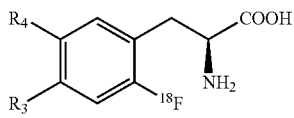

wherein:
$R_3=R_4=OH$
$R_3=H$; $R_4=OH$ or
$R_3=OH$; $R_4=H$ by the acid hydrolysis with mineral acids, such as HCl, HBr or HI, using dry heating or microwave heating of protected F-18 labeled chiral analog s having the formula

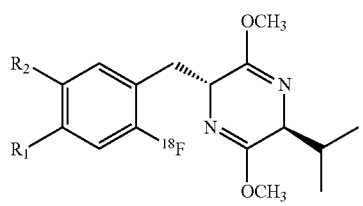

wherein:
$R_1=R_2=OCH_2Ph$, $OCOOC(CH_3)_3$, $OCH_3$ or
R1=H; $R_2=OCH_2Ph$, $OCOOC(CH_3)_3$, $OCH_3$ or
$R_1=OCH_2Ph$, $OCOOC(CH_3)_3$, $OCH_3$; $R_2=H$ Example 13 is representative of such a reaction scheme.

EXAMPLE 13

FIG. 8 shows the reaction scheme for the synthesis of specific oxoimidazolidine and pyrazine based iodonium ylide precursors a) 3,4-Dibenzyloxybenzyl alcohol (28)

3,4-Dibenzyloxybenzaldehyde (27) (22.0 mmol) was suspended in 100 mL of anhydrous methanol and cooled to 0° C. under argon. Sodium borohydride (33.0 mmol) was added in portions to the suspension and stirred for 1 h at the same temperature. The resulting solution was then stirred at room temperature overnight. The reaction mixture was evaporated to dryness and the residue was dissolved in ice-water and neutralized with HCl. The solution was then extracted with chloroform and the organic layer was washed successively with water, 10% $NaHCO_3$ solution in water and brine. The organic layer was dried over anhydrous $Na_2SO_4$, filtered and evaporated to dryness to provide pure 3,4-Dibenzyloxybenzyl alcohol (28) in 97.5% yield.

$^1$H NMR ($CDCl_3$): δ 7.29-7.52 (m, 10H, ArH), 7.02 (d, 1H, ArH), 6.86-6.95 (dt, 2H, ArH), 5.19 (d, 4H), 4.59 (d, 2H).

b) 3,4-Dibenzyloxy-6-iodobenzyl alcohol (29)

The dibenzyloxybenzyl alcohol 28 (21.44 mmol) and silver trifluoroacetate (21.44 mmol) were suspended in 100 mL of dry chloroform and stirred under argon. A solution of iodine (21.44 mmol) in dry chloroform (50 mL) was added to the suspension dropwise at room temperature. The reaction mixture was then stirred for a further period of 2 h and filtered. The filtrate was washed with 20% sodium thiosulfate solution in water. The organic layer was separated and dried over anhydrous $Na_2SO_4$. Filtration was followed by evaporation of the chloroform solution resulting in the pure iodo compound, 3,4-Dibenzyloxy-6-iodobenzyl alcohol (29), as a pale yellow solid in 84% yield.

$^1$H NMR ($CDCl_3$): δ 7.29-7.49 (m, 11H, ArH), 7.10 (s, 1H, ArH), 5.15 (d, 4H), 4.59 (s, 2H).

MS (MALDI): Calcd for $C_{21}H_{19}IO_3$ ($M^+$): 446.04. Found: 468.98 ($M^++Na$).

c) 3,4-Dibenzyloxy-6-iodobenzyl bromide (30)

A solution of the dibenzyloxy iodo alcohol derivative 29 (18.04 mmol) in 100 mL of dichloromethane was added dropwise to an ice-cold hydrobromic acid (47-49% in water, (72 mL) over a period of 90 min. The resulting yellow mixture was stirred for 30 min and then warmed slowly to room temperature. The reaction mixture was diluted with water and extracted with dichloromethane. The organic phase was dried over anhydrous $Na_2SO_4$, filtered and evaporated to provide the bromo product, 3,4-Dibenzyloxy-6-iodobenzyl bromide (30) in quantitative yield.

$^1$H NMR ($CDCl_3$): δ 7.32-7.48 (m, 11H, ArH), 7.07 (s, 1H, ArH), 5.15 (d, 4H), 4.54 (s, 2H).

d) (2S,5S)-tert-Butyl-5-(2'-iodo-4',5'-dibenzyloxybenzyl)-2-tert-butyl-3-methyl-4-oxoimidazolidine-1-carboxylate (31)

The carboxylate 31 was obtained using the general procedure reported in the literature [(D. Seebach, E. Dziadulewicz, L. Behrendt, S. Cantoreggi, R. Fitzi, "Synthesis of Nonproteinogenic (R)- or (S)-Amino Acids Analogues of Phenylalanine, Isotopically Labelled and Cyclic Amino Acids from tert-Butyl 2-(tert-Butyl)-3-methyl-4-oxo-1-imidazolidinecarboxylate (Boc-BMI)." *Liebigs Ann. Chem.*, pp 1215-1232 (1989)]. Thus, diisopropylamine (2.2 mmol) dissolved in dry THF (4 mL) was cooled to −40° C. under argon and a solution of BuLi (2.5 M in hexane, 2.2 mmol) was added drop wise. After 30 min of stirring at −40° C., a solution of (S)-tert-butyl-2-tert-butyl-3-methyl-4-oxoimidazolidine-1-carboxylate (2.2 mmol) was added drop wise and the reaction mixture was stirred for 30 min at −40° C. A solution of the benzyl bromide (30) (2.2 mmol) in dry THF (6 mL) was then added drop wise to the reaction mixture. The new reaction mixture was stirred for 3 h at the same temperature and then poured into a saturated solution of $NH_4Cl$. The product was extracted with EtOAc and the organic layer was washed with $NaHCO_3$ solution followed by brine. The organic phase was dried over anhydrous $Na_2SO_4$, filtered and evaporated to afford a yellow oil. Flash chromatographic purification of the oily product on a silica gel column with 6:1 hexane:ethyl acetate mixture provided pure (2S,5S)-tert-butyl-5-(2'-iodo-4',5'-dibenzyloxybenzyl)-2-tert-butyl-3-methyl-4-oxoimidazolidine-1-carboxylate (31) as a white solid in 32% yield.

$^1$H NMR ($CDCl_3$): δ 7.32-7.44 (m, 11H, ArH), 6.60 (s, 1H, ArH), 5.09 (s, 4H), 4.95 (s, 1H), 4.3 (t, 1H), 3.44 (dd, 2H), 2.8 (s, 3H), 1.31 (s, 9H), 0.98 (s, 9H).

MS (MALDI): Calcd for $C_{34}H_{41}IN_2O_5$ ($M^+$): 684.21. Found: 707.07 ($M^++Na$).

2,2-Dimethyl-4,6-dioxo-1,3-dioxane iodonium ylide derivative 33

The iodo oxoimidazolidine derivative 31 (0.22 mmol) was first oxidized with dimethyldioxirane in the presence of acetic acid as described above to afford the corresponding diacetoxy intermediate analog in 84% yield.

$^1$H NMR (CDCl$_3$): δ 7.76 (d, 1H, ArH), 7.47-7.36 (m, 10H, ArH), 7.05 (d, 1H, ArH), 5.08-5.15 (m, 4H), 4.95 (s, 1H), 4.3 (t, 1H), 3.44 (dd, 2H), 3.03 (s, 3H), 2.11 (s, 6H,), 1.01 (s, 9H), 0.95 (s, 9H).

This diacetoxyiodo intermediate derivative can subsequently be converted to the iodonium ylide 33 using the procedure given for the preparation of the analog 20.

2,5-Dihydro-3,6-dimethoxy-2-isopropyl-5-(2'-iodo-4',5'-dibenzyloxybenzyl)-(2R,5S)-pyrazine (32)

The diastereomeric product 32 was obtained by a reaction of the lithium salt of the chiral auxiliary (2R)-2,5-dihydro-3,6-dimethoxy-2-isopropylpyrazine with the bromo derivative 30 using a modification of a procedure reported in the literature [U. Schollkopf, "Enantioselective Synthesis of Non-Proteinogenic Amino Acids via Metallated Bis-Lactim Ethers of 2,5-Diketopiperazines." Tetrahedron, 39, pp 2085-2091 (1983)]. Specifically, (2R)-2,5-dihydro-3,6-dimethoxy-2-isopropylpyrazine (15.7 mmol) was dissolved in 10 mL of THF (freshly distilled from LiAlH$_4$). The light yellow solution was cooled to −78° C. (dry ice/acetone bath) and stirred for 15 min under argon. A 2.5 M solution of n-butyl lithium (15.7 mmol) was added drop wise over a period of 10 min and the mixture was stirred for 20 min at −78° C. In a separate flask CuCN (7.86 mmol) was stirred with 10 mL of freshly distilled THF at room temperature for 10 min. The white suspension was then cooled to 0° C. (ice bath) and stirred at that temperature for 20 min. The n-BuLi reaction mixture was then transferred to the white suspension of CuCN/THF under argon using a cannula. The resulting yellow suspension turned into a yellow solution within two minutes. The reaction mixture was then stirred at 0° C. for 15 min and cooled to −78° C. After 15 min of stirring at −78° C., a solution of bromo derivative 30 (7.86 mmol) in 20 mL of freshly distilled THF was added drop wise. The color of the reaction mixture changed to greenish brown. After stirring for a further period of 2 h at −78° C., the reaction mixture was warmed gradually to room temperature. The reaction mixture was then poured into a saturated solution of NH$_4$Cl and extracted with EtOAc. The organic phase was dried over anhydrous Na$_2$SO$_4$, filtered and evaporated to afford an oily compound which was purified by silica gel flash column chromatography eluting with 5% ethyl acetate in hexane to yield pure 2,5-dihydro-3,6-dimethoxy-2-isopropyl-5-(2'-iodo-4',5'-dibenzyloxybenzyl)-(2R,5S)-pyrazine (32) as a white solid in 70% yield.

2,2-Dimethyl-4,6-dioxo-1,3-dioxane iodonium ylide derivative 34

This ylide derivative can also be prepared from the iodo product 32, first by oxidizing it with DMDO reagent in the presence of acetic acid to give the corresponding diacetoxyiodo product which upon reaction with 2,2-dimethyl-4,6-dioxo-1,3-dioxane as described above will provide the analog, 2,2-Dimethyl-4,6-dioxo-1,3-dioxane iodonium ylide derivative 34.

The iodonium ylides 26, 33 and 34 can then be used as precursor materials for the preparation of 6-[F-18]fluoro-L-dopa in the manner described above. They can then be reacted with [F-18] fluoride ion as described above. The F-18 labeled intermediates upon acid hydrolysis will yield 6-[F-18]fluoro-L-dopa. Further, the F-18 fluorinated D- and L-chiral amino acids can be prepared by starting with the appropriate D- and L-chiral precursors.

We claim:

1. A procedure for preparing an F-18 labeled aryl derivative comprising:

replacing an iodonium ylide group of a benzene derivative containing an iodonium ylide group with a no-carrier-added F-18 fluoride ion wherein the benzene derivative containing an iodonium ylide group is selected from the group consisting of:

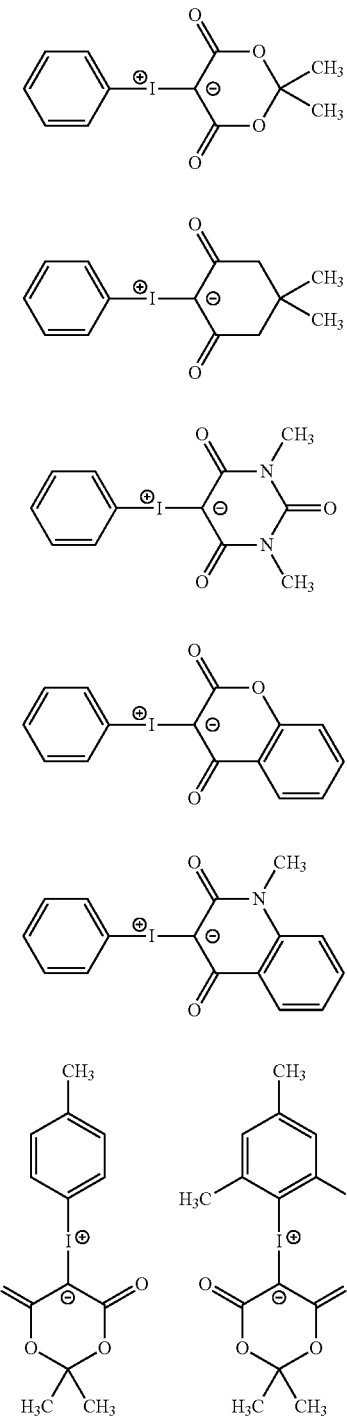

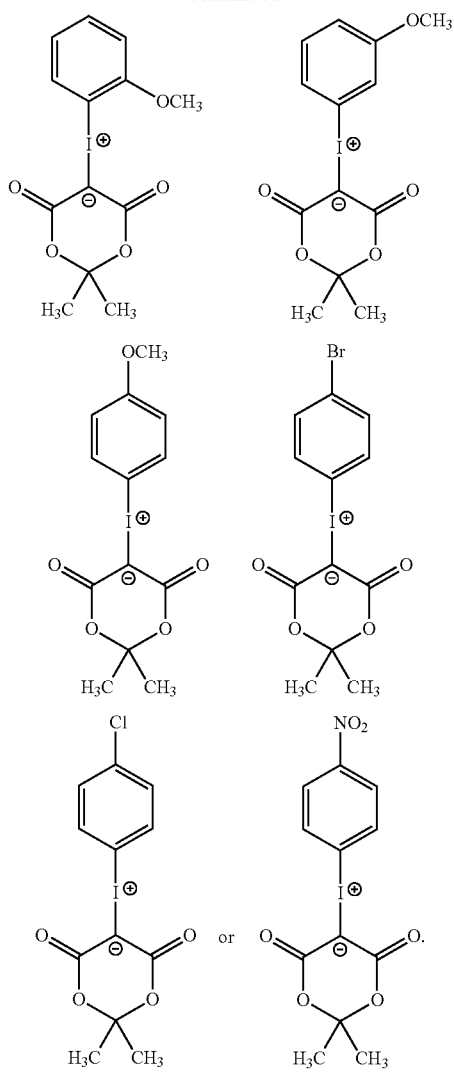
2. The procedure of claim 1 wherein the benzene derivative containing an iodonium ylide group is listed in the left hand column of the table below and the F-18 containing derivative produced therefrom is listed in the corresponding right hand column of the table below:

-continued

| Phenyl iodonium ylide | Product |
|---|---|
| (4-OCH₃-phenyl iodonium ylide of 2,2-dimethyl-1,3-dioxane-4,6-dione) | 4-[¹⁸F]fluoroanisole |
| (4-Br-phenyl iodonium ylide of 2,2-dimethyl-1,3-dioxane-4,6-dione) | 4-[¹⁸F]fluorobromobenzene |
| (4-Cl-phenyl iodonium ylide of 2,2-dimethyl-1,3-dioxane-4,6-dione) | 4-[¹⁸F]fluorochlorobenzene |
| (4-NO₂-phenyl iodonium ylide of 2,2-dimethyl-1,3-dioxane-4,6-dione) | 4-[¹⁸F]fluoronitrobenzene |

3. The procedure of claim 1 wherein the no-carrier-added [F-18]fluoride ion is produced by proton bombardment of [O-18]water in a cyclotron body.

4. The procedure of claim 3 wherein:

an aqueous solution containing the [F-18]fluoride ion is treated with potassium carbonate and a ligand or tetraalkylammonium bicarbonate, and the treated solution is evaporated to dryness to form a dry composition containing an [F-18]fluoride ion labeled compounds.

5. The procedure of claims 4 wherein the dry composition containing [F-18]fluoride ion labeled compounds is reacted with the benzene derivative containing an iodonium ylide group to form an [F-18] fluoroaryl derivative.

6. The procedure of claim 5 wherein the [F-18]fluoroaryl derivative is purified to produce a >95% radiochemically pure [F-18]fluoroaryl derivative.

7. The procedure of claim 5 wherein the [F-18]fluoroaryl derivative is purified to produce a >99% radiochemically and chemically pure product.

8. 2,2-Dimethyl-4,6-dioxo-1,3-dioxan-5-[N-di(tert-butoxycarbonyl)-3,4-di-(tert-butoxycarbonyloxy)-L-phenylalanine ethyl ester-6-iodonium]ylide.

9. A process for producing 2,2-dimethyl-4,6-dioxo-1,3-dioxan-5[N-di(tert-butoxycarbonyl)-3,4-di-(tert-butoxycarbonyloxy)-L-phenylalanine ethyl ester-6-iodonium]ylide comprising:

(a) forming N-di(tert-butoxycarbonyl)-3,4-di-(tert-butoxycarbonyloxy)-6-iodo-L-phenylalanine ethyl ester by reacting N-(tert-butoxycarbonyl)-3,4-di-(tert-butoxycarbonyloxy)-6-iodo-L-phenylalanine ethyl ester with di-tert-butyldicarbonate, (b) reacting the product of step a) above with dimethyldioxirane in acetone-acetic acid mixture to form N-di(tert-butoxycarbonyl)-3,4-di-(tert-butoxycarbonyloxy)-6-(diacetoxy)iodo-L-phenylalanine ethyl ester, and (c) exposing the product of step b) above to 2,2-dimethyl-4,6-dioxo-1,3-dioxane to form 2,2-dimethyl-4,6-dioxo-1,3-dioxan-5-[N-di(tert-butoxycarbonyl)-3,4-di-(tert-butoxycarbonyloxy)-L-phenylalanine ethyl ester-6-iodonium]ylide.

10. A process for forming 6-[F-18]fluoro-L-dopa comprising:

(a) preparing an F-18 labeled aryl derivative from a compound containing a benzene ring with a pendant iodonium ylide group comprising:

replacing the iodonium ylide group with a no-carrier-added F-18 fluoride ion, said no-carrier-added [F-18] fluoride ion being produced by proton bombardment of [O-18]water in a cyclotron body, treating an aqueous solution containing the [F-18]fluoride ion with potassium carbonate and a ligand or tetraalkylammonium bicarbonate, and evaporating the treated solution to dryness to form a dry composition containing an [F-18]fluoride ion labeled compounds.

(b) reacting 2,2-dimethyl-4,6-dioxo-1,3-dioxan-5-[N-di(tert-butoxycarbonyl)-3,4-di-(tert-butoxycarbonyloxy)-L-phenylalanine ethyl ester-6-iodonium]ylide with the dry composition containing the [F-18]fluoride ion labeled compounds, and (c) treating the product of step b) above with a halogen acid.

11. A compound having the formula:

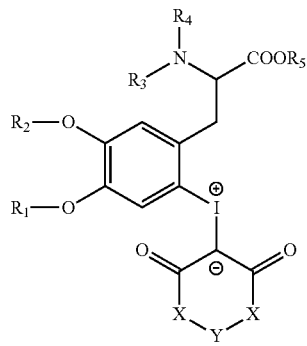

wherein $R_1$ and $R_2$ are hydroxyl protecting lower alkyl groups or benzyl or tert-butoxycarbonyl groups, $R_3$ and $R_4$ are amine protecting acetoxy, trifluoroacetoxy or tert-butoxycarbonyloxy groups, $R_5$ is carboxylic acid protecting methyl, ethyl, tert-butyl, or benzyl groups, $X=CH_2$, O, S, $NCH_3$ or $NCH_2Ph$ and $Y=CH_2$, $C(CH_3)_2$ or $C=O$.

12. The compound of claim 11 where $R_1$ and $R_2$ are $(CH_3)_3COCO$, $R_3$ and $R_4$ are $(CH_3)_3COCO$, $X=O$ and $Y=C(CH_3)_2$.

13. A procedure for the preparation of iodonium ylide analogs having the formula:

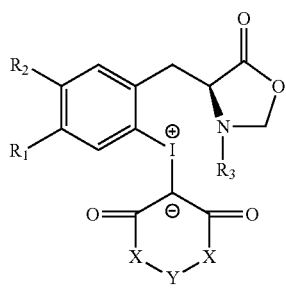

wherein:

$R_1=R_2=R_3=OCOOC(CH_3)_3$, or $R_1=R_2=OCOOC(CH_3)_3$ or $OCH_3$ and $R_3=COCH_3$ or $COOCH_2Ph$, or $R_1=H; R_2=OCOOC(CH_3)$ or $OCH_3$ and $R_3=COCH_3$ or, $COOCH_2Ph$, or $R_1=OCOOC(CH_3)_3$ or $OCH_3$; $R_2=H$ and $R_3=COCH_3$ or $COOCH_2Ph$, $X=CH_2$, O, S, $NCH_3$ or $NCH_2Ph$ and $Y=CH_2$, $C(CH_3)_2$ or $=O$ comprising:

hydrolyzing an ester group in a protected L-iododopa or L-iodotyrosine analogs, cyclizing an amino acid group therein, oxidizing an iodo group therein into a diacetoxyiodo moiety and subsequently reacting the resultant compound with a cyclo 1,3-dicarbonyl derivative.

14. A method for the production of F-18 chiral analogs having the formula:

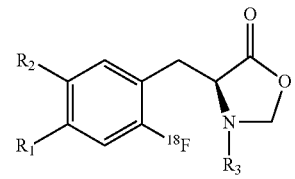

comprising the nucleophilic substitution of an iodonium ylide group in a chiral derivative having the formula

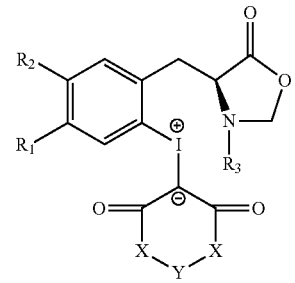

wherein:

$R_1=R_2=R_3=OCOOC(CH_3)_3$, or $R_1=R_2=OCOOC(CH_3)_3$ or $OCH_3$ and $R_3=COCH_3$ or $COOCH_2Ph$, or $R_1=H; R_2=OCOOC(CH_3)_3$ or $OCH_3$ and $R_3$ $COCH_3$ or $COOCH_2Ph$ or $R_1=OCOOC(CH_3)_3$ or $OCH_3$; $R_2=H$ and $R_3=COCH_3$ or $COOCH_2Ph$, $X=CH_2$, O, S, $NCH_3$ or $NCH_2Ph$ and $Y=CH_2$ or $C(CH_3)_2$, $=O$ using dry heating or microwave heating for the nucleophilic substitution of the iodonium ylide group in said chiral derivative, providing a dry, anhydrous no-carrier-added F-18 fluoride ion, said F-18 fluoride ion being derived from a [F-18]KF/Kryptofix complex, [F-18]CsF or quaternary ammonium fluoride, the quaternary ammonium groups being selected from tetramethyl, tetraethyl, tetra n-butyl, and tetrabenzyl.

15. A procedure for the preparation of iodonium ylide derivatives having the formula

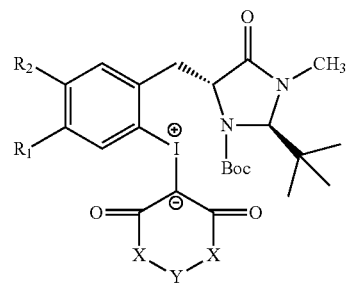

wherein:

$R_1=R_2=OCH_2Ph$, $OCOOC(CH_3)_3$ or $OCH_3$, or $R1=H$ and $R_2=OCH_2Ph$, $OCOOC(CH_3)_3$ or $OCH_3$, or $R_1=OCH_2Ph$, $OCOOC(CH_3)_3$ or $OCH_3$ and $R_2=H$ $X=CH_2$, O, S, $NCH_3$ or $NCH_2Ph$ and $Y=CH_2$, $C(CH_3)_2$ or $=O$ comprising reacting:

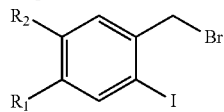

with a chiral oxoimdazolidine auxiliary to produce a protected chiral amino acid derivatives, reacting the resultant compound with dimethyldioxirane in the presence of acetic acid to produce a diacetoxyiodo analog and subsequently reacting the diacetoxyiodo analog with a cyclo1,3-dicarbonyl derivative.

16. A method for the production of F-18 chiral compounds having the formula

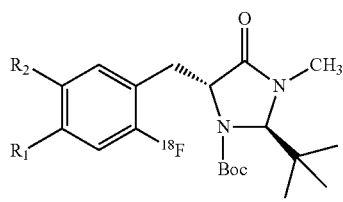

comprising the nucleophilic substitution of the iodonium ylide group in a chiral derivative having the formula

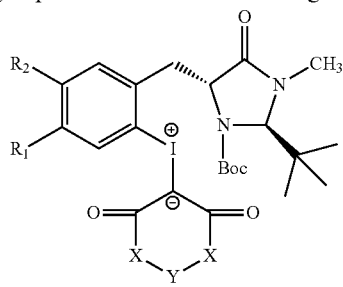

with dry/anhydrous no-carrier-added F-18 fluoride ion using dry heating or microwave heating where the F-18 fluoride ion is derived from [F-18]KF/Kryptofix complex, [F-18]CsF or quaternary ammonium fluoride, the quaternary ammonium group being selected from tetramethyl, tetraethyl, tetra n-butyl, or tetrabenzyl and $R_1=R_2=OCH_2Ph$, $OCOOC(CH_3)_3$ or $OCH_3$ or
R1=H and $R_2=OCH_2Ph$, $OCOOC(CH_3)_3$ or $OCH_3$, or
$R_1=OCH_2Ph$, $OCOOC(CH_3)_3$ or $OCH_3$ and $R_2=H$
$X=CH_2$, O, S, $NCH_3$ or $NCH_2Ph$ and
$Y=CH_2$, $C(CH_3)_2$ or =O.

17. A procedure for the preparation of the iodonium ylides having the formula

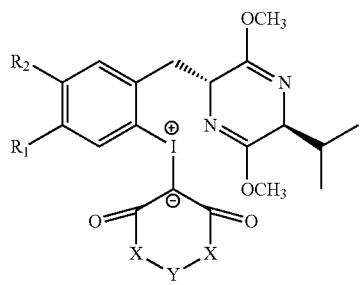

comprising:
reacting

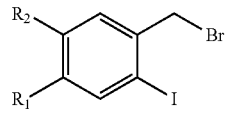

with a chiral pyrazine auxiliary to produce protected chiral amino acid derivatives, reacting the resultant compound with dimethyldioxirane in the presence of acetic acid to produce a diacetoxyiodo analog and subsequently reacting the diacetoxyiodo analog with the cyclo1,3-dicarbonyl derivatives wherein:

$R_1=R_2=OCH_2Ph$, $OCOOC(CH_3)_3$ or $OCH_3$ or
R1=H and $R_2=OCH_2Ph$, $OCOOC(CH_3)_3$ or $OCH_3$ or
$R_1=OCH_2Ph$, $OCOOC(CH_3)_3$ or $OCH_3$ and $R_2=H$
$X=CH_2$, O, S, $NCH_3$ or, $NCH_2Ph$ and
$Y=CH_2$, $C(CH_3)_2$ or =O.

18. A method for the production of F-18 chiral analogs having the formula

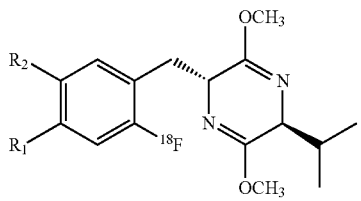

comprising the nucleophilic substitution of the iodonium ylide group in a chiral analog having the formula:

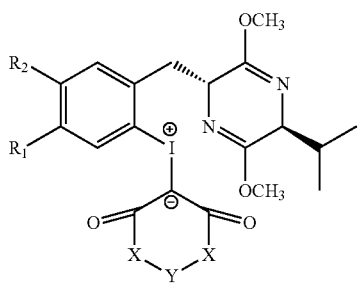

with dry/anhydrous no-carrier-added F-18 fluoride ion using dry heating or microwave heating where the F-18 fluoride ion is derived from [F-18]KF/Kryptofix complex, [F-18]CsF or quaternary ammonium fluoride, the quaternary ammonium groups selected from tetramethyl, tetraethyl, tetra n-butyl, and tetrabenzyl wherein $R_1=R_2=OCH_2Ph$, $OCOOC(CH_3)_3$ or $OCH_3$ or
R1=H and $R_2=OCH_2Ph$, $OCOOC(CH_3)_3$ or $OCH_3$ or
$R_1=OCH_2Ph$, $OCOOC(CH_3)_3$ or $OCH_3$ and $R_2=H$
$X=CH_2$, O, S, $NCH_3$ or $NCH_2Ph$ and
$Y=CH_2$, $C(CH_3)_2$ or =O.

19. The processes of claim 9 for the preparation of
a) iodonium ylide containing amino acids having a D-configuration comprising utilizing D-chiral precursors, or
b) iodonium ylide containing amino acids having an L-configuration comprising utilizing-L-chiral precursors.

20. The methods of claim 14 for the preparation of
a) iodonium ylide containing amino acids having a D-configuration comprising utilizing D-chiral precursors, or
b) iodonium ylide containing amino acids having an L-configuration comprising utilizing-L-chiral precursors.

21. The methods of claim 16 for the preparation of
a) iodonium ylide containing amino acids having a D-configuration comprising utilizing D-chiral precursors, or
b) iodonium ylide containing amino acids having an L-configuration comprising utilizing-L-chiral precursors.

22. The methods of claim 18 for the preparation of
a) iodonium ylide containing amino acids having a D-configuration comprising utilizing D-chiral precursors, or
b) iodonium ylide containing amino acids having an L-configuration comprising utilizing-L-chiral precursors.

* * * * *